United States Patent
Niemeyer

(10) Patent No.: US 6,772,053 B2
(45) Date of Patent: *Aug. 3, 2004

(54) ASPECTS OF A CONTROL SYSTEM OF A MINIMALLY INVASIVE SURGICAL APPARATUS

(75) Inventor: Günter D. Niemeyer, Mountain View, CA (US)

(73) Assignee: Visx, Incorporated, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/269,336

(22) Filed: Oct. 11, 2002

(65) Prior Publication Data

US 2003/0029463 A1 Feb. 13, 2003

Related U.S. Application Data

(63) Continuation of application No. 09/288,068, filed on Apr. 7, 1999, now Pat. No. 6,493,608.
(60) Provisional application No. 60/111,710, filed on Dec. 8, 1988, provisional application No. 60/111,713, filed on Dec. 8, 1998, provisional application No. 60/111,711, filed on Dec. 8, 1998, provisional application No. 60/111,714, filed on Dec. 8, 1998, and provisional application No. 60/116,842, filed on Jan. 22, 1999.

(51) Int. Cl.[7] ............................................... G05D 1/10
(52) U.S. Cl. ..................... 700/302; 700/255; 700/256; 700/257; 700/251; 700/263; 700/61; 700/65; 700/63; 606/130
(58) Field of Search ................................. 700/302, 255, 700/256, 257, 251, 263, 61, 65, 63; 606/130

(56) References Cited

U.S. PATENT DOCUMENTS 1,418,184 A 5/1922 Trunick
2,815,697 A 12/1957 Saunders-Singer
2,901,258 A 8/1959 Brandafi (List continued on next page.)

FOREIGN PATENT DOCUMENTS

| CH | 482 439 A | 1/1970 |
| DE | 2819976 A1 | 11/1979 |
| DE | 3806190 A1 | 9/1988 |

(List continued on next page.)

OTHER PUBLICATIONS

"Another Pair of Hands for Surgeon?" 1972, The Blue Cross magazine Perspective, p. 27.
Alexander, A.D.III, "Impacts of Telemation on Modern Society", *, 1st CISM–IFTO MM Symposium, vol. 2, pp. 122–136. (Sep. 1973).
Asada Haruhiko et al., "Development of a Direct–Drive Arm Using High Torque Brushless Motors," Chapter 7, pp. 583–599.

(List continued on next page.)

*Primary Examiner*—Ramesh Patel
*Assistant Examiner*—Thomas Pham
(74) *Attorney, Agent, or Firm*—Townsend&Townsend& CrewLLP; Mark D. Barrish, Esq.

(57) ABSTRACT

A surgical method and a control system is provided. The surgical method and the control system can advantageously be used in a minimally invasive surgical apparatus. The method includes generating a desired surgical instrument movement command signal. It further includes comparing the desired surgical instrument movement command signal with at least one preset surgical instrument movement limitation. Should the desired surgical instrument command signal transgress the preset surgical instrument movement limitation, the desired surgical instrument movement command signal is restricted to yield a restricted surgical instrument movement command signal. A surgical instrument is then caused to move in response to the restricted surgical instrument movement command signal. The method further provides for haptic feedback on a master control in response to restriction of the desired surgical instrument movement command signal.

10 Claims, 25 Drawing Sheets

U.S. PATENT DOCUMENTS

| | | | |
|---|---|---|---|
| 3,145,333 A | | 8/1964 | Pardini et al. |
| 3,463,329 A | | 8/1969 | Gartner |
| 3,818,125 A | | 6/1974 | Butterfield |
| 3,921,445 A | | 11/1975 | Hill et al. |
| 3,923,166 A | | 12/1975 | Fletcher et al. |
| 3,934,201 A | | 1/1976 | Majetski |
| 4,113,115 A | | 9/1978 | Yoshio |
| 4,260,319 A | | 4/1981 | Motoda et al. |
| 4,264,266 A | | 4/1981 | Trechsel |
| 4,349,837 A | | 9/1982 | Hinds |
| 4,419,041 A | | 12/1983 | Rose |
| 4,510,574 A | | 4/1985 | Guittet et al. |
| 4,562,463 A | | 12/1985 | Lipton |
| 4,582,067 A | | 4/1986 | Silberstein et al. |
| 4,583,117 A | | 4/1986 | Lipton et al. |
| 4,594,671 A | * | 6/1986 | Sugimoto et al. ............ 700/263 |
| 4,623,971 A | * | 11/1986 | Ailman et al. .............. 700/252 |
| 4,636,138 A | | 1/1987 | Gorman |
| 4,651,201 A | | 3/1987 | Schoolman |
| 4,716,350 A | * | 12/1987 | Huang et al. ............... 700/256 |
| 4,734,866 A | * | 3/1988 | Bartelt et al. ............... 700/256 |
| 4,744,363 A | | 5/1988 | Hasson |
| 4,750,475 A | | 6/1988 | Yoshihashi |
| 4,751,925 A | | 6/1988 | Tontarra |
| 4,762,455 A | | 8/1988 | Coughlan et al. |
| 4,808,898 A | | 2/1989 | Pearson |
| 4,837,734 A | | 6/1989 | Ichikawa et al. |
| 4,855,822 A | | 8/1989 | Narendra et al. |
| 4,862,873 A | | 9/1989 | Yajima et al. |
| 4,873,572 A | | 10/1989 | Miyazaki et al. |
| 4,899,730 A | | 2/1990 | Stennert et al. |
| 4,922,338 A | | 5/1990 | Arpino |
| 4,941,106 A | | 7/1990 | Krieger |
| 4,942,538 A | * | 7/1990 | Yuan et al. ................. 700/259 |
| 4,942,539 A | | 7/1990 | McGee et al. |
| 4,947,702 A | | 8/1990 | Kato |
| 5,002,418 A | | 3/1991 | McCown et al. |
| 5,020,933 A | | 6/1991 | Salvestro et al. |
| 5,045,936 A | | 9/1991 | Lobb et al. |
| 5,060,532 A | | 10/1991 | Barker |
| 5,062,761 A | | 11/1991 | Glachet |
| 5,072,361 A | * | 12/1991 | Davis et al. .................. 700/65 |
| 5,078,140 A | | 1/1992 | Kwoh |
| 5,096,236 A | | 3/1992 | Thony |
| 5,141,519 A | | 8/1992 | Smith et al. |
| 5,142,930 A | | 9/1992 | Allen et al. |
| 5,159,249 A | * | 10/1992 | Megherbi ................ 318/568.1 |
| 5,187,796 A | * | 2/1993 | Wang et al. .................... 712/4 |
| 5,206,930 A | * | 4/1993 | Ishikawa et al. ............ 700/260 |
| 5,209,747 A | | 5/1993 | Knoepfler |
| 5,219,351 A | | 6/1993 | Teubner et al. |
| 5,236,432 A | | 8/1993 | Matsen, III et al. |
| 5,253,706 A | | 10/1993 | Reid |
| 5,257,998 A | | 11/1993 | Ota et al. |
| 5,260,319 A | | 11/1993 | Effland et al. |
| 5,264,266 A | | 11/1993 | Yokoyama et al. |
| 5,273,039 A | | 12/1993 | Fujiwara et al. |
| 5,279,309 A | | 1/1994 | Taylor et al. |
| 5,281,220 A | | 1/1994 | Blake, III |
| 5,284,130 A | | 2/1994 | Ratliff |
| 5,299,288 A | * | 3/1994 | Glassman et al. .......... 700/245 |
| 5,325,866 A | | 7/1994 | Krzyzanowski |
| 5,339,799 A | * | 8/1994 | Kami et al. ................. 600/117 |
| 5,343,385 A | * | 8/1994 | Joskowicz et al. ............ 700/57 |
| 5,397,323 A | | 3/1995 | Taylor et al. |
| 5,425,528 A | | 6/1995 | Rains et al. |
| 5,441,505 A | | 8/1995 | Nakamura |
| 5,474,566 A | | 12/1995 | Alesi et al. |
| 5,480,409 A | | 1/1996 | Riza |
| 5,590,034 A | * | 12/1996 | Snell ........................... 700/61 |
| 5,625,576 A | * | 4/1997 | Massie et al. .................. 703/6 |
| 5,629,594 A | * | 5/1997 | Jacobus et al. ........ 318/568.11 |
| 5,631,973 A | * | 5/1997 | Green ......................... 382/128 |
| 5,636,138 A | | 6/1997 | Gilbert et al. |
| 5,691,898 A | * | 11/1997 | Rosenberg et al. ............ 700/85 |
| 5,695,500 A | * | 12/1997 | Taylor et al. ................ 606/130 |
| 5,749,362 A | * | 5/1998 | Funda et al. ................ 600/407 |
| 5,762,458 A | * | 6/1998 | Wang et al. .................... 414/1 |
| 5,841,950 A | * | 11/1998 | Wang et al. ................ 700/264 |
| 5,855,583 A | * | 1/1999 | Wang et al. ........... 318/568.11 |
| 5,876,325 A | * | 3/1999 | Mizuno et al. ............. 600/102 |
| 5,878,193 A | * | 3/1999 | Wang et al. ................ 700/251 |
| 5,923,139 A | * | 7/1999 | Colgate et al. ............. 318/566 |
| 6,219,589 B1 | * | 4/2001 | Faraz et al. ................. 700/254 |
| 6,233,504 B1 | * | 5/2001 | Das et al. ................... 700/260 |
| 6,470,236 B2 | * | 10/2002 | Ohtsuki ...................... 700/247 |
| 6,493,608 B1 | * | 12/2002 | Niemeyer ................... 700/302 |
| 2001/0016804 A1 | * | 8/2001 | Cunningham et al. ......... 703/7 |

FOREIGN PATENT DOCUMENTS

| | | |
|---|---|---|
| DE | 4213426 A1 | 10/1992 |
| EP | 0 239 409 A1 | 9/1987 |
| EP | 0 291 292 B1 | 11/1988 |
| EP | 0 595 291 B1 | 4/1997 |
| FR | 2460762 A1 | 1/1981 |
| GB | 2040134 A | 8/1980 |
| GB | 2117732 A | 3/1983 |
| WO | WO 92/16141 A1 | 10/1992 |
| WO | WO 96/09587 | 3/1996 |
| WO | WO 97/29690 | 8/1997 |
| WO | WO 97/43942 | 11/1997 |
| WO | WO 97/43943 | 11/1997 |
| WO | WO 97/49340 | 12/1997 |

OTHER PUBLICATIONS

Bejczy, A.K. et al, "Controlling Remote Manipulators Through Kinesthetic Coupling", 1983, Computers in Mechanical Engineering, pp. 48–60.

Fisher, S. "Virtual Interface Environment", 1986, Proceedings IEEE/AIAA 7th Digital Avionics Systems Conference, pp. 346–350.

Guerrouad A. et al., "S.M.O.S.: Stereotaxical Microelemanipulator for Ocular Surgery," IEEE Engineering in Medicine & Biology Society, 11th Annual International Conference, 1989, Medical Applications of Robotics, Track 16: Biorobotics, pp. 879–880.

Held, R. and Durlach, N. et al., "Telepresence, Time Delay and Adaptation", *, Spatial Displays and Spatial Instruments Proceedings of a Conference sponsored by NASA Ames Research Center and the School of Optometry, Univ. of California, pp. 28–1 through 28–16.

Jau, B..M., "Anthropomorphic Remoter Manipulator", 1991, NASA Tech Briefs, p. 92. (Apr. 1991).

Kazerooni H., "Design and Analysis of the Statically Balanced Direct–Drive Robot Manipulator", Robotics & Computer–Integrated Manufacturing, 1989, vol. 6, No. 4, pp. 287–293.

Kim et al., "A Helmet Mounted Display for Telerobotics", 1988 33 IEEE Computer Society International Conference, California, pp. 543–547.

Lazarevic, "Feasibility of a Stewart Platform with Fixed Actuators as a Platform for CABG Sugery Device" Master's Thesis, Columbia University, Department of Bioengineering, pp. 1–45.

Matsushima, K. and Koyanagi, H., "Servo Micro Manipulator Tiny Micro Mark–1", 1982, 4th Symposium on Theory and Practice of Robots and Manipulators, pp. 193–201.

Ng. W. S. et al., "Robotic Surgery," IEEE Engineering in Medicine and Biology, Mar. 1993, pp. 120–125.

R. Richter, "Telesurgery may Bridge Future Gaps", Times Tribune, Sunday, Jan. 24, pp. A–1 and A–16.

Schenker et al., "Development of telemanipular for dexterity enhanced mirosurgery" Second Annual International Symposium on Medical Robotics and Computer Assisted Surgery, Nov. 4–7, 1995, Baltimore, Maryland, USA, pp. 81–88.

Spain, E.H. "Stereo Advantage for a Peg–In Hole–Task Using Force–Feedback Manipulator", 1990, Stereoscopic Displays and Applications, pp. 244–254.

Tachi et al., "Tele–existence Master Slave System for Remote Manipulation", 1990, Proceedings of the 29th Conference on Decision and Control, vol. 1 of 6, pp. 85–90.

Taubes Gary, "Surgery in Cyberspace," Discover, Dec. 1994, pp. 85–92.

Taylor Russell H. et al., "A Telerobotic Assistant for Laparoscopic Surgery," Engineering in Medicine and Biology, May–Jun. 1995, pp. 279–288.

Trevelyan James P. et al., "Motion Control for a Sheep Shearing Robot," IEEE Robotics Research Conference, the 1st International Symposium, Carroll, NH, USA, Conference Date: Aug. 25, 1983, Conference No. 05357, Publication by MIT Press, pp. 175–190.

World Wide Web document entitled"Jet Propulsion Laboratory" printed May 13, 1999, http://robotics.jpl.nasa.gov/people/hayati/Quarterly_Reports/FY96Q3/jpl/jpl.html.

* cited by examiner

ASPECTS OF A CONTROL SYSTEM OF A MINIMALLY INVASIVE SURGICAL APPARATUS

CROSS-REFERENCES TO RELATED APPLICATIONS

The present application is a continuation patent application of U.S. patent application Ser. No. 09/288,068 filed Apr. 7, 1999, now U.S. Pat. No. 6,493,608, the full disclosure of which is incorporated herein by reference.

This application is related to the following patents and patent applications, the full disclosures of which are incorporated herein by reference: PCT International Application No. PCT/US98/19508, entitled "Robotic Apparatus," filed on Sep. 18, 1998, U.S. Application Serial No. 60/111,710, entitled "Master Having Redundant Degrees of Freedom," filed on Dec. 8, 1998, U.S. Application Serial No. 60/111,713, entitled "Surgical Robotic Tools, Data Architecture, and Use," filed on Dec. 8, 1998; U.S. Application Serial No. 60/111,711, entitled "Image-Shifting for a Telerobotic System," filed on Dec. 8, 1998; U.S. Application Serial No. 60/111,714, entitled "Stereo Viewer System for Use in Telerobotic Systems", filed on Dec. 8, 1998; U.S. Application Serial No. 60/116,842, entitled "Repositioning and Reorientation of Master/Slave Relationship in Minimally Invasive Telesurgery," filed on Jan. 22, 1999; and U.S. Pat. No. 5,808,665, entitled "Endoscopic Surgical Instrument and Method for Use," issued on Sep. 15, 1998; the full disclosures of which are incorporated herein by reference.

BACKGROUND OF THE INVENTION

Minimally invasive medical techniques are aimed at reducing the amount of extraneous tissue which is damaged during diagnostic or surgical procedures, thereby reducing patient recovery time, discomfort, and deleterious side effects. Millions of surgeries are performed each year in the United States. Many of these surgeries can potentially be performed in a minimally invasive manner. However, only a relatively small number of surgeries currently use these techniques due to limitations in minimally invasive surgical instruments and techniques and the additional surgical training required to master them.

Advances in minimally invasive surgical technology could dramatically increase the number of surgeries performed in a minimally invasive manner. The average length of a hospital stay for a standard surgery is significantly longer than the average length for the equivalent surgery performed in a minimally invasive surgical manner. Thus, the complete adoption of minimally invasive techniques could save millions of hospital days, and consequently millions of dollars annually in hospital residency costs alone. Patient recovery times, patient discomfort, surgical side effects, and time away from work are also reduced with minimally invasive surgery.

The most common form of minimally invasive surgery is endoscopy. Probably the most common form of endoscopy is laparoscopy, which is minimally invasive inspection and surgery inside the abdominal cavity. In standard laparoscopic surgery, a patient's abdomen is insufflated with gas, and cannula sleeves are passed through small (approximately ½ inch) incisions to provide entry ports for laparoscopic surgical instruments.

The laparoscopic surgical instruments generally include a laparoscope for viewing the surgical field, and working tools defining end effectors. Typical surgical end effectors include clamps, graspers, scissors, staplers, or needle holders, for example. The working tools are similar to those used in conventional (open) surgery, except that the working end or end effector of each tool is separated from its handle by, e.g., an approximately 12-inch long, extension tube.

To perform surgical procedures, the surgeon passes these working tools or instruments through the cannula sleeves to a required internal surgical site and manipulates them from outside the abdomen by sliding them in and out through the cannula sleeves, rotating them in the cannula sleeves, levering (i.e., pivoting) the instruments against the abdominal wall and actuating end effectors on the distal ends of the instruments from outside the abdomen. The instruments pivot around centers defined by the incisions which extend through muscles of the abdominal wall. The surgeon monitors the procedure by means of a television monitor which displays an image of the surgical site via a laparoscopic camera. The laparoscopic camera is also introduced through the abdominal wall and into the surgical site. Similar endoscopic techniques are employed in, e.g., arthroscopy, retroperitoneoscopy, pelviscopy, nephroscopy, cystoscopy, cisternoscopy, sinoscopy, hysteroscopy, urethroscopy and the like.

There are many disadvantages relating to current minimally invasive surgical (MIS) technology. For example, existing MIS instruments deny the surgeon the flexibility of tool placement found in open surgery. Most current laparoscopic tools have rigid shafts and difficulty is experienced in approaching the surgical site through the small incision. Additionally, the length and construction of many surgical instruments reduces the surgeon's ability to feel forces exerted by tissues and organs on the end effector of the associated tool. The lack of dexterity and sensitivity of surgical tools is a major impediment to the expansion of minimally invasive surgery.

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control devices, at the remote location, which control the motion of servomechanically operated instruments.

The servomechanism used for telesurgery will often accept input from two master controllers (one for each of the surgeon's hands), and may include two robotic arms. Operative communication between each master control and an associated arm and instrument assembly is achieved through a control system. The control system includes at least one processor which relays input commands from a master controller to an associated arm and instrument assembly and from the arm and instrument assembly to the associated master controller in the case of, e.g., force feedback.

With advances in computer technology, it is now possible for processors to accept and interpret the wide range of quite rapid, precise hand motions made by a surgeon in manipulating the master controllers during surgery. Unfortunately, robotic arms often have responsive limitations which may be more restrictive than the controller. Furthermore, the robotic arm joints often have limits in their displacement capability or range of achievable position relative to each other. Yet further, the robotic arm and surgical instrument assemblies may have positional limits beyond which it is not possible to move.

It would be advantageous that master control movements and responsive end effector movements as displayed be as natural and comfortable to the surgeon as possible. To achieve this, certain obstacles should be overcome. One such obstacle is constraining master control movement input within bounds dictated by mechanically achievable positional movements and velocity of its associated arm and surgical instrument assembly.

It is an object of this invention to provide a method and control system whereby master control movement can be constrained to remain within limitations imposed by its associated robotic arm and instrument assembly, in an intuitive manner.

It is to be appreciated that although the method and control system of the invention is described with reference to a minimally invasive surgical apparatus in this specification, the application of the invention is not to be limited to this application only, but can be used in any type of apparatus where an input is entered at one location and a corresponding movement is required at a remote location and in which it is required, or merely beneficial, to constrain master control input to remain within limitations or constraints dictated by the corresponding movement at the remote location. Thus, the invention may find application in the fields of satellite dish tracking, handling hazardous substances, to name but two of many possible qualifying fields.

BRIEF SUMMARY OF THE INVENTION

According to one aspect of the invention, there is provided a surgical method including generating a desired surgical instrument movement command signal; comparing the desired surgical instrument movement command signal with at least one preset surgical instrument movement limitation; restricting the desired surgical instrument movement command signal to yield a restricted surgical instrument movement command signal should the desired surgical instrument movement command signal transgress the preset surgical instrument movement limitation; and causing a surgical instrument to move in response to the restricted surgical instrument movement command signal.

According to another aspect of the invention, there is provided a control system including processing means arranged to generate a desired surgical instrument movement command signal; and processing means arranged to compare the desired surgical instrument movement command signal with at least one preset surgical instrument movement limitation, and to restrict the desired surgical instrument movement command signal to yield a restricted surgical instrument movement command signal should the desired surgical instrument command signal transgress the preset surgical instrument movement limitation.

In accordance with another aspect of the invention, there is provided a method of effecting control between a master and a slave of a minimally invasive surgical apparatus, the method including generating slave movement commands in response to and corresponding with master movement; inputting the slave movement commands into a simulated domain, the simulated domain having at least one preset movement limitation; determining whether or not the slave movement command transgresses the movement limitation in the simulated domain; restricting the slave movement command in the simulated domain, if it transgresses the limitation, by a value calculated to yield a restricted slave movement command not transgressing the movement limitation; forwarding the restricted slave movement command to the slave to cause the slave to move in sympathy with the restricted slave movement command; and causing a master movement command, corresponding to the value by which the slave movement command was restricted, to be sent to the master to cause the master to resist movement promoting corresponding slave movement commands which transgress the slave movement limitation set in the simulated domain.

In accordance with yet a further aspect of the invention, there is provided a control system for effecting control between a master and a slave of a minimally invasive surgical apparatus, the control system including generating means for generating slave movement commands in response to and corresponding with master movement; a simulated domain into which the slave movement commands are input prior to the slave movement commands being forwarded to the slave; at least one movement limitation set in the simulated domain; restriction means in the simulated domain for restricting the slave movement commands, should they transgress the limitation, by a calculated value so as to yield a restricted slave movement command which does not transgress the limitation; communication means for communicating the restricted slave movement command to the slave to cause the slave to move in sympathy with the restricted slave movement command; and feedback means whereby a master movement command signal, corresponding to the calculated value by which the slave movement command was restricted, is sent to the master to cause the master to resist movement promoting corresponding slave movement commands which transgress the slave movement limitation set in the simulated domain According to another aspect of the invention, there is provided a method of transforming a velocity signal relative to a reference coordinate system into joint space by means of a transformation relationship, the method including modifying the transformation relationship to account for at least one singularity.

BRIEF DESCRIPTION OF THE DRAWINGS

The invention will now be described, by way of example, and with reference to the accompanying diagrammatic drawings, in which.

DETAILED DESCRIPTION OF THE INVENTION

Figures 1A, 1B:
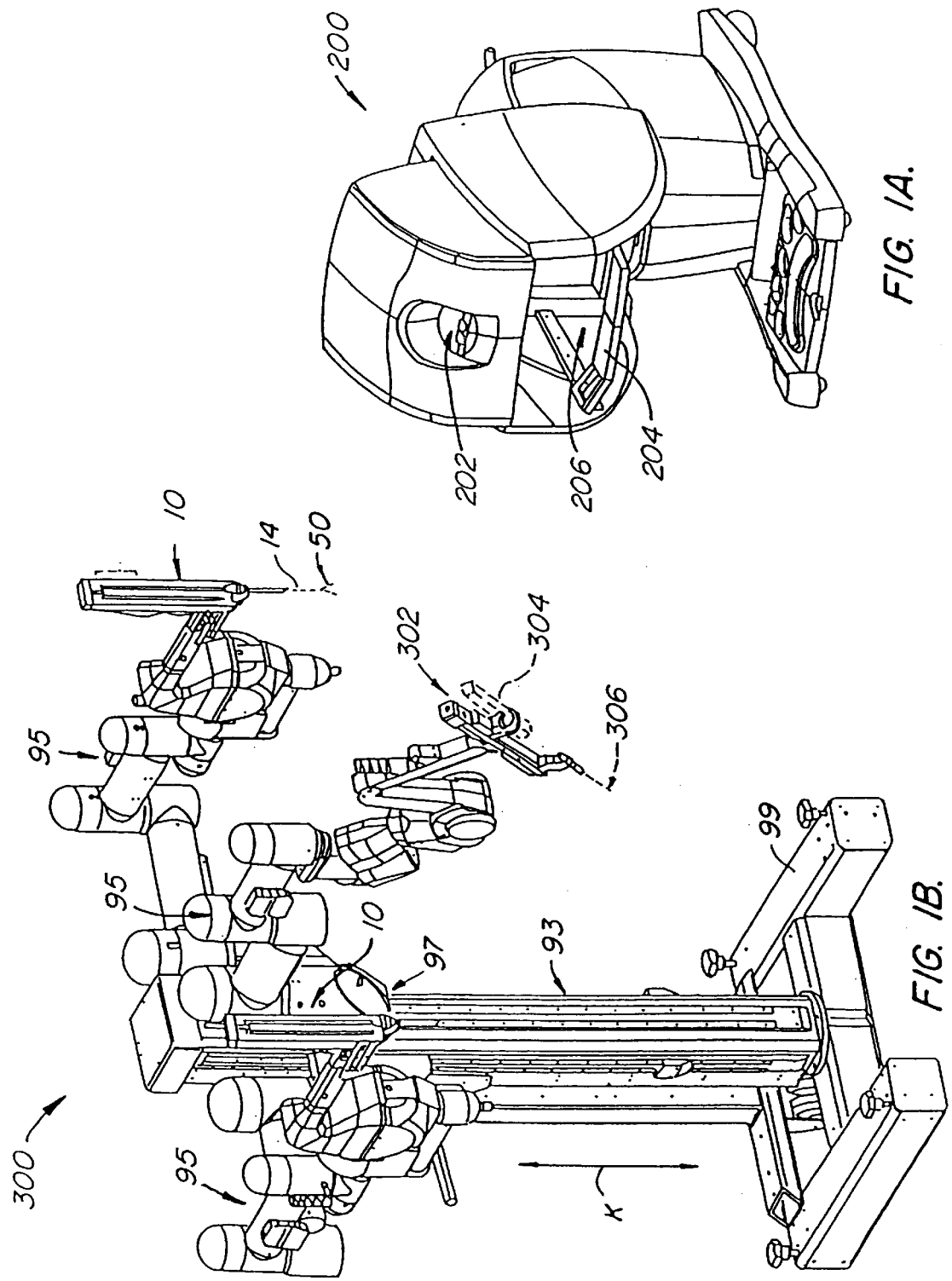
FIG. 1A shows a three-dimensional view of an operator station of a telesurgical system in accordance with the invention.
FIG. 1B shows a three-dimensional view of a cart or surgical station of the telesurgical system, the cart carrying three robotically controlled arms, the movement of the arms being remotely controllable from the operator station shown in FIG. 1A.

Referring to FIG. 1A of the drawings, an operator station or surgeon's console of a minimally invasive telesurgical system is generally indicated by reference numeral 200. The station 200 includes a viewer 202 where an image of a surgical site is displayed in use. A support 204 is provided on which an operator, typically a surgeon, can rest his or her forearms while gripping two master controls (not shown in FIG. 1A), one in each hand. The master controls are positioned in a space 206 inwardly beyond the support 204. When using the control station 200, the surgeon typically sits in a chair in front of the control station 200, positions his or her eyes in front of the viewer 202 and grips the master controls one in each hand while resting his or her forearms on the support 204.

In FIG. 1B of the drawings, a cart or surgical station of the telesurgical system is generally indicated by reference numeral 300. In use, the cart 300 is positioned close to a patient requiring surgery and is then normally caused to remain stationary until a surgical procedure to be performed has been completed. The cart 300 typically has wheels or castors to render it mobile. The station 200 is typically positioned remote from the cart 300 and can be separated from the cart 300 by a great distance, even miles away, but will typically be used within an operating room with the cart 300.

The cart 300 typically carries three robotic arm assemblies. One of the robotic arm assemblies, indicated by reference numeral 302, is arranged to hold an image capturing device 304, e.g., an endoscope, or the like. Each of the two other arm assemblies 10, 10 respectively, includes a surgical instrument 14. The endoscope 304 has a viewing end 306 at a remote end of an elongate shaft thereof. It will be appreciated that the endoscope 304 has an elongate shaft to permit its viewing end 306 to be inserted through an entry port into an internal surgical site of a patient's body. The endoscope 304 is operatively connected to the viewer 202 to display an image captured at its viewing end 306 on the viewer 202. Each robotic arm assembly 10, 10 is normally operatively connected to one of the master controls. Thus, the movement of the robotic arm assemblies 10, 10 is controlled by manipulation of the master controls. The instruments 14 of the robotic arm assemblies 10, 10 have end effectors which are mounted on wrist members which are pivotally mounted on distal ends of elongate shafts of the instruments 14, as is described in greater detail hereinbelow. It will be appreciated that the instruments 14 have elongate shafts to permit the end effectors to be inserted through entry ports into the internal surgical site of a patient's body. Movement of the end effectors relative to the ends of the shafts of the instruments 14 is also controlled by the master controls.

The robotic arms 10, 10, 302 are mounted on a carriage 97 by means of setup joint arms 95. The carriage 97 can be adjusted selectively to vary its height relative to a base 99 of the cart 300, as indicated by arrows K. The setup joint arms 95 are arranged to enable the lateral positions and orientations of the arms 10, 10, 302 to be varied relative to a vertically extending column 93 of the cart 300. Accordingly, the positions, orientations and heights of the arms 10, 10, 302 can be adjusted to facilitate passing the elongate shafts of the instruments 14 and the endoscope 304 through the entry ports to desired positions relative to the surgical site. When the surgical instruments 14 and endoscope 304 are so positioned, the setup joint arms 95 and carriage 97 are typically locked in position.

Figure 2A:
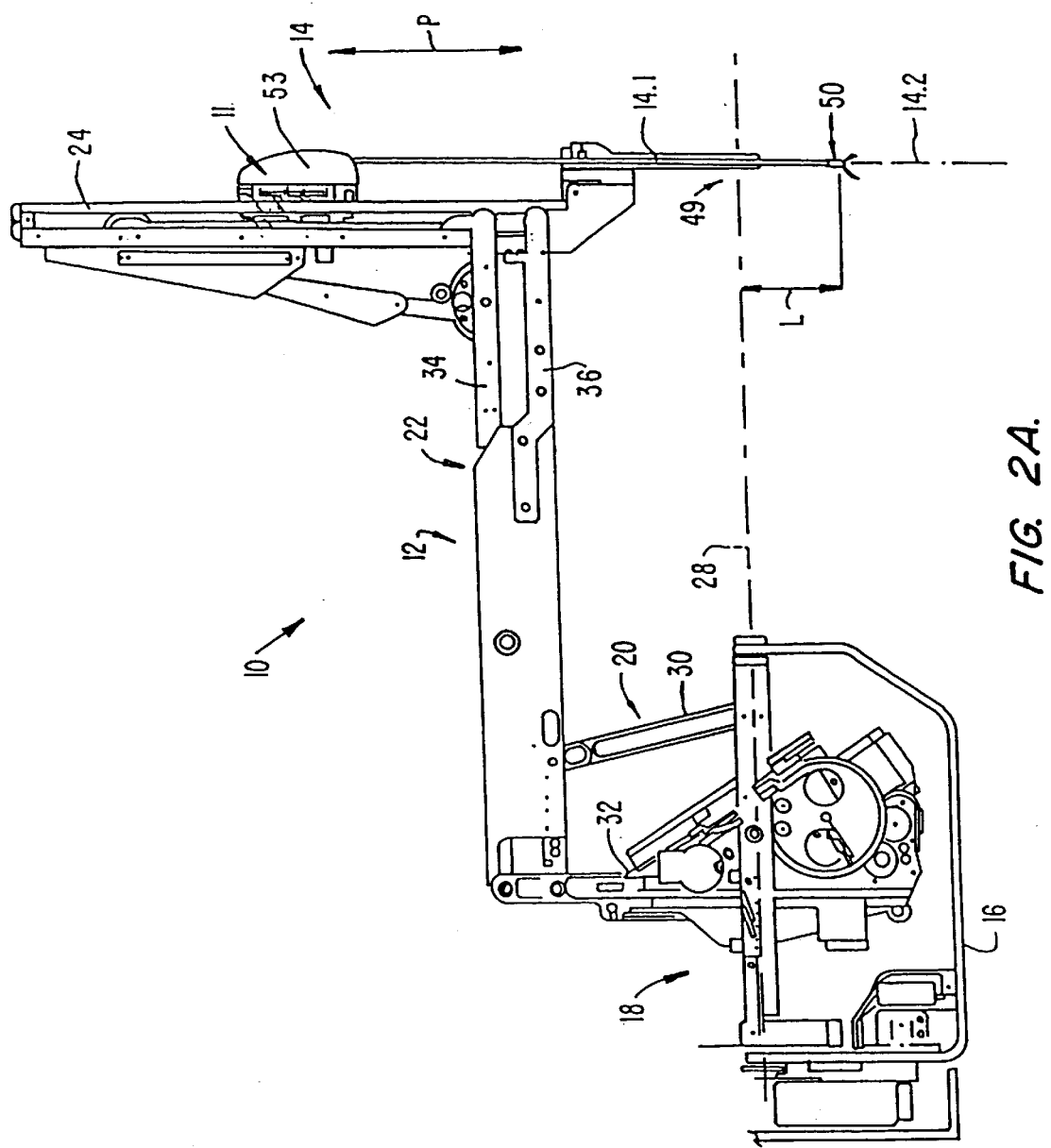
FIG. 2A shows a side view of a robotic arm and surgical instrument assembly.
Figure 2B:
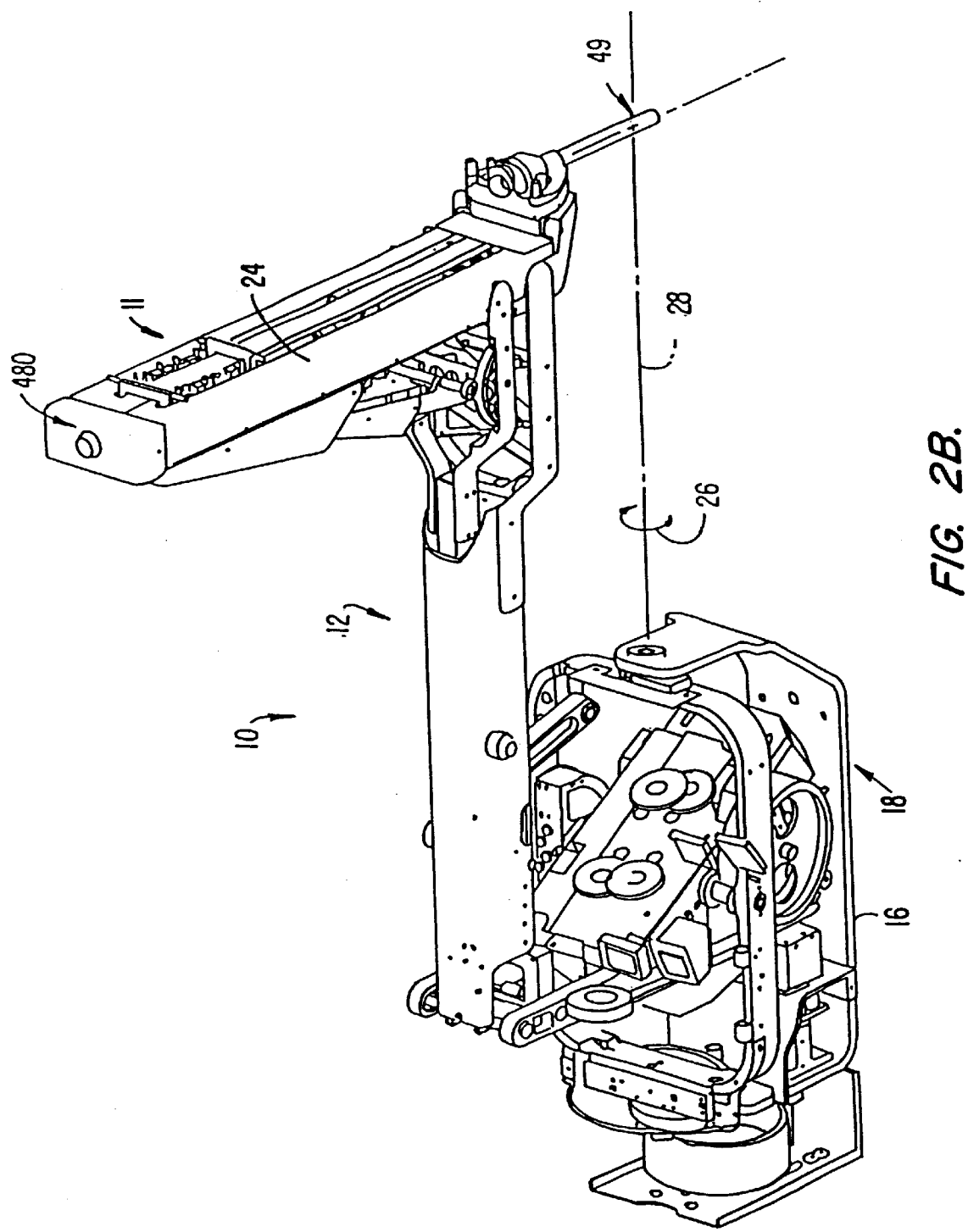
FIG. 2B shows a three-dimensional view corresponding to FIG. 2A.
Figure 3:
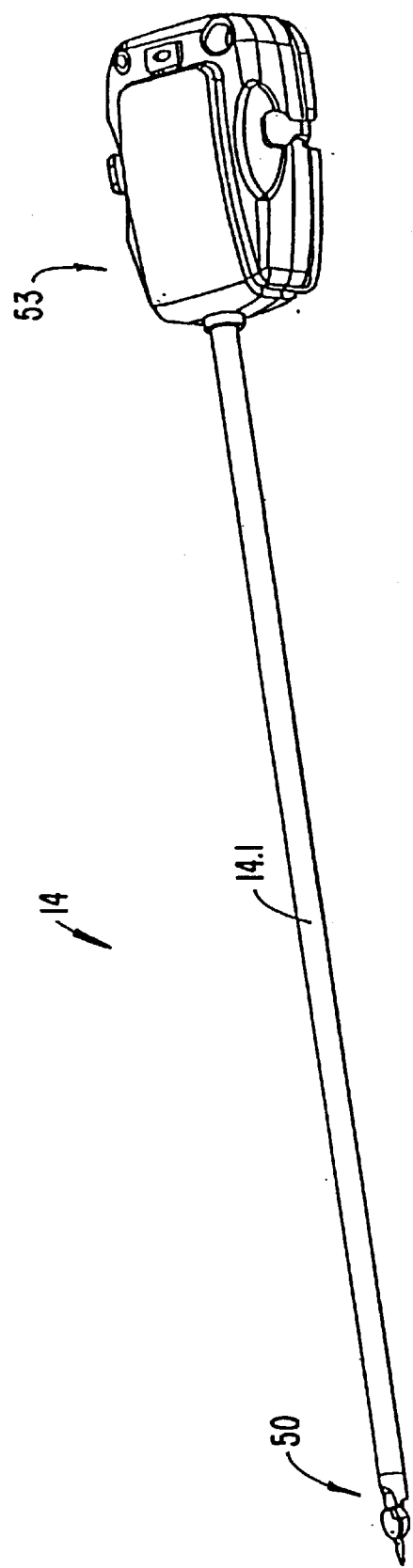
FIG. 3 shows a three-dimensional view of a surgical instrument.

In FIGS. 2A and 2B of the drawings, one of the robotic arm assemblies 10 is shown in greater detail. Each assembly 10 includes an articulated robotic arm 12, and a surgical instrument, schematically and generally indicated by reference numeral 14, mounted thereon. FIG. 3 indicates the general appearance of the surgical instrument 14 in greater detail.

The surgical instrument 14 includes an elongate shaft 14.1. The wrist-like mechanism, generally indicated by reference numeral 50, is located at a working end of the shaft 14.1. A housing 53, arranged releasably to couple the instrument 14 to the robotic arm 12, is located at an opposed end of the shaft 14.1. In FIG. 2A, and when the instrument 14 is coupled or mounted on the robotic arm 12, the shaft 14.1 extends along an axis indicated at 14.2. The instrument 14 is typically releasably mounted on a carriage 11, which can be driven to translate along a linear guide formation 24 of the arm 12 in the direction of arrows P The robotic arm 12 is typically mounted on a base or platform at an end of its associated setup joint arm 95 by means of a bracket or mounting plate 16.

The robotic arm 12 includes a cradle, generally indicated at 18, an upper arm portion 20, a forearm portion 22 and the guide formation 24. The cradle 18 is pivotally mounted on the plate 16 in a gimbaled fashion to permit rocking movement of the cradle 18 in the direction of arrows 26 as shown in FIG. 2B, about a pivot axis 28. The upper arm portion 20 includes link members 30, 32 and the forearm portion 22 includes link members 34, 36. The link members 30, 32 are pivotally mounted on the cradle 18 and are pivotally connected to the link members 34, 36. The link members 34, 36 are pivotally connected to the guide formation 24. The pivotal connections between the link members 30, 32, 34, 36, the cradle 18, and the guide formation 24 are arranged to constrain the robotic arm 12 to move in a specific manner. The movement of the robotic arm 12 is illustrated schematically in FIG. 4.

Figure 4:
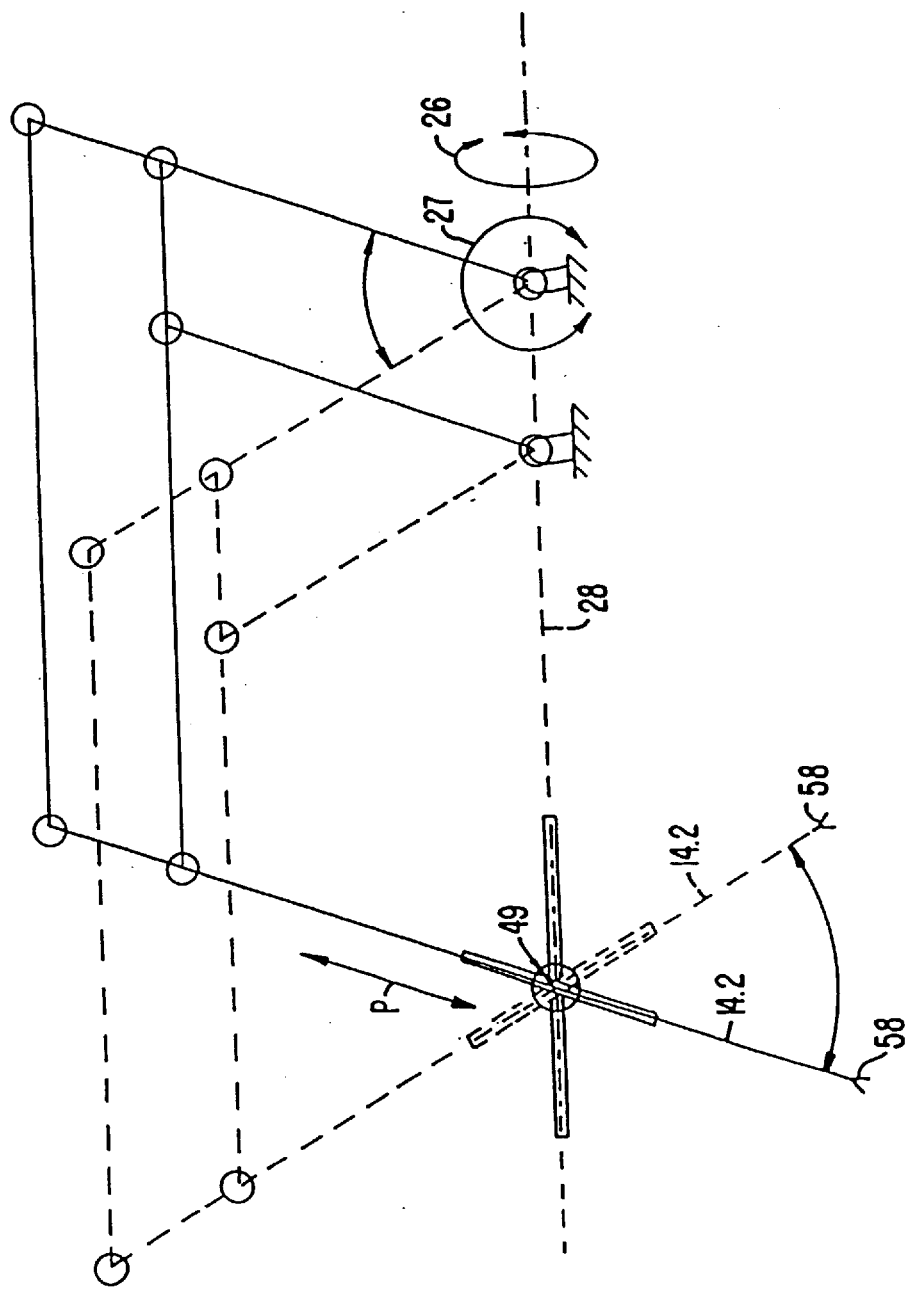
FIG. 4 shows a schematic kinematic diagram corresponding to the side view of the robotic arm shown in FIG. 2A, and indicates the arm having been displaced from one position into another position.

With reference to FIG. 4, the solid lines schematically indicate one position of the robotic arm and the dashed lines indicate another possible position into which the arm can be displaced from the position indicated in solid lines.

It will be understood that the axis 14.2 along which the shaft 14.1 of the instrument 14 extends when mounted on the robotic arm 12 pivots about a pivot center or fulcrum 49. Thus, irrespective of the movement of the robotic arm 12, the pivot center 49 normally remains in the same position relative to the stationary cart 300 on which the aim 12 is mounted. In use, the pivot center 49 is positioned at a port of entry into a patient's body when an internal surgical procedure is to be performed. It will be appreciated that the shaft 14.1 extends through such a port of entry, the wrist-like mechanism 50 then being positioned inside the patient's body. Thus, the general position of the mechanism 50 relative to the surgical site in a patient's body can be changed by movement of the arm 12. Since the pivot center 49 is coincident with the port of entry, such movement of the arm does not excessively effect the surrounding tissue at the port of entry.

As can best be seen with reference to FIG. 4, the robotic arm 12 provides three degrees of freedom of movement to the surgical instrument 14 when mounted thereon. These degrees of freedom of movement are firstly the gimbaled motion indicated by arrows 26, pivoting or pitching movement as indicated by arrows 27 and the linear displacement in the direction of arrows P. Movement of the arm as indicated by arrows 26, 27 and P is controlled by appropriately positioned actuators, e.g., electrical motors, or the like, which respond to inputs from its associated master control to drive the arm 12 to a required position as dictated by movement of the master control. Appropriately positioned sensors, e.g., potentiometers, encoders, or the like, are provided on the arm and its associated setup joint arm 95 to enable a control system of the minimally invasive telesurgical system to determine joint positions, as described in greater detail hereinbelow. It will be appreciated that whenever "sensors" are referred to in this specification, the term is to be interpreted widely to include any appropriate sensors such as positional sensors, velocity sensors, or the like. It will be appreciated that by causing the robotic arm 12 selectively to displace from one position to another, the general position of the wrist-like mechanism 50 at the surgical site can be varied during the performance of a surgical procedure.

Figure 5:
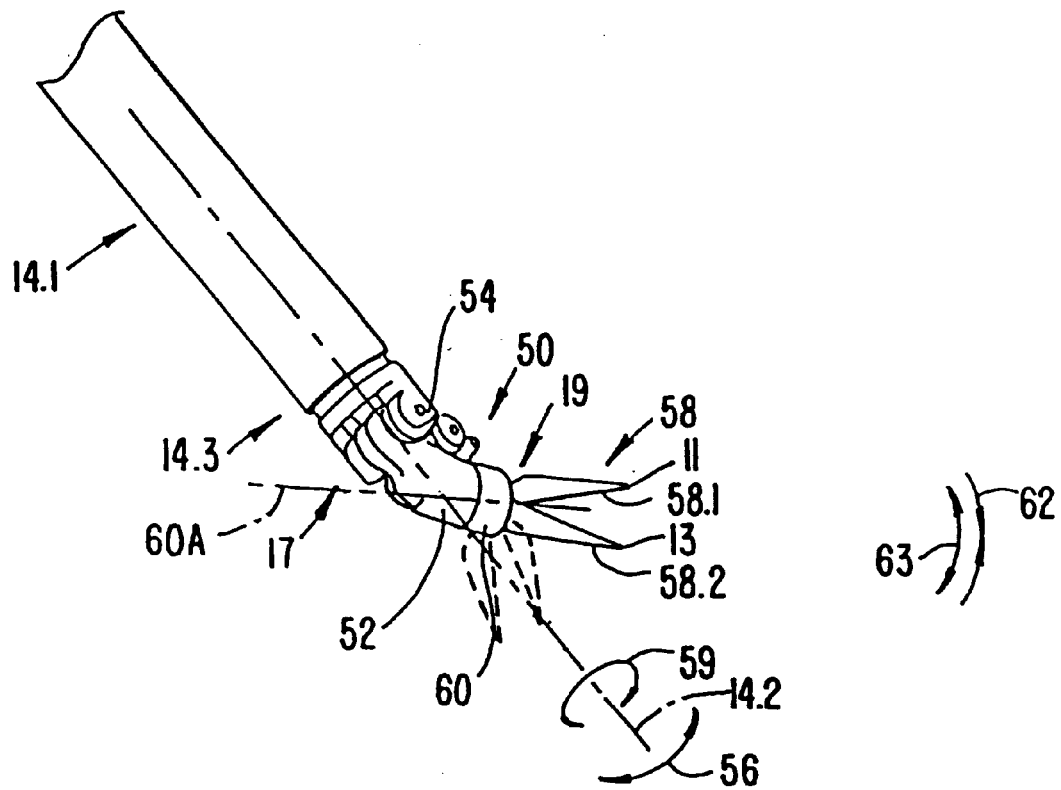
FIG. 5 shows, at an enlarged scale, a wrist member and end effector of the surgical instrument shown in FIG. 3, the wrist member and end effector being movably mounted on a working end of a shaft of the surgical instrument.

Referring now to FIG. 5 of the drawings, the wrist-like mechanism 50 will now be described in greater detail. In FIG. 5, the working end of the shaft 14.1 is indicated at 14.3. The wrist-like mechanism 50 includes a wrist member 52. One end portion of the wrist member 52 is pivotally mounted in a clevis, generally indicated at 17, on the end 14.3 of the shaft 14.1 by means of a pivotal connection 54. The wrist member 52 can pivot in the direction of arrows 56 about the pivotal connection 54. An end effector, generally indicated by reference numeral 58, is pivotally mounted on an opposed end of the wrist member 52. The end effector 58 is in the form of, e.g., a clip applier for anchoring clips during a surgical procedure. Accordingly, the end effector 58 has two parts 58.1, 58.2 together defining a jaw-like arrangement.

It will be appreciated that the end effector can be in the form of any required surgical tool, e.g., having two members or fingers which pivot relative to each other, such as scissors, pliers for use as needle drivers, or the like. Instead, it can include a single working member, e.g., a scalpel, cautery electrode, or the like. When a tool other than a clip applier is required during the surgical procedure, the tool 14 is simply removed from its associated arm and replaced with an instrument bearing the required end effector, e.g., a scissors, or pliers, or the like.

The end effector 58 is pivotally mounted in a clevis, generally indicated by reference numeral 19, on an opposed end of the wrist member 52, by means of a pivotal connection 60. It will be appreciated that flee ends 11, 13 of the parts 58.1, 58.2 are angularly displaceable about the pivotal connection 60 toward and away from each other as indicated by arrows 62, 63. It will further be appreciated that the members 58.1,58.2 can be displaced angularly about the pivotal connection 60 to change the orientation of the end effector 58 as a whole, relative to the wrist member 52. Thus, each part 58.1, 58.2 is angularly displaceable about the pivotal connection 60 independently of the other, so that the end effector 58, as a whole, is angularly displaceable about the pivotal connection 60 as indicated in dashed lines in FIG. 5. Furthermore, the shaft 14.1 is rotatably mounted on the housing 53 for rotation as indicated by the arrows 59. Thus, the end effector 58 has three degrees of freedom of movement relative to the arm 12, namely, rotation about the axis 14.2 as indicated by arrows 59, angular displacement as a whole about the pivot 60 and angular displacement about the pivot 54 as indicated by arrows 56. By moving the end effector within its three degrees of freedom of movement, its orientation relative to the end 14.3 of the shaft 14.1 can selectively be varied. It will be appreciated that movement of the end effector relative to the end 14.3 of the shaft 14.1 is controlled by appropriately positioned actuators, e.g., electrical motors, or the like, which respond to inputs from the associated master control to drive the end effector 58 to a required orientation as dictated by movement of the master control. Furthermore, appropriately positioned sensors, e.g., encoders, or potentiometers, or the like, are provided to permit the control system of the minimally invasive telesurgical system to determine joint positions as described in greater detail hereinbelow.

Figure 6A:
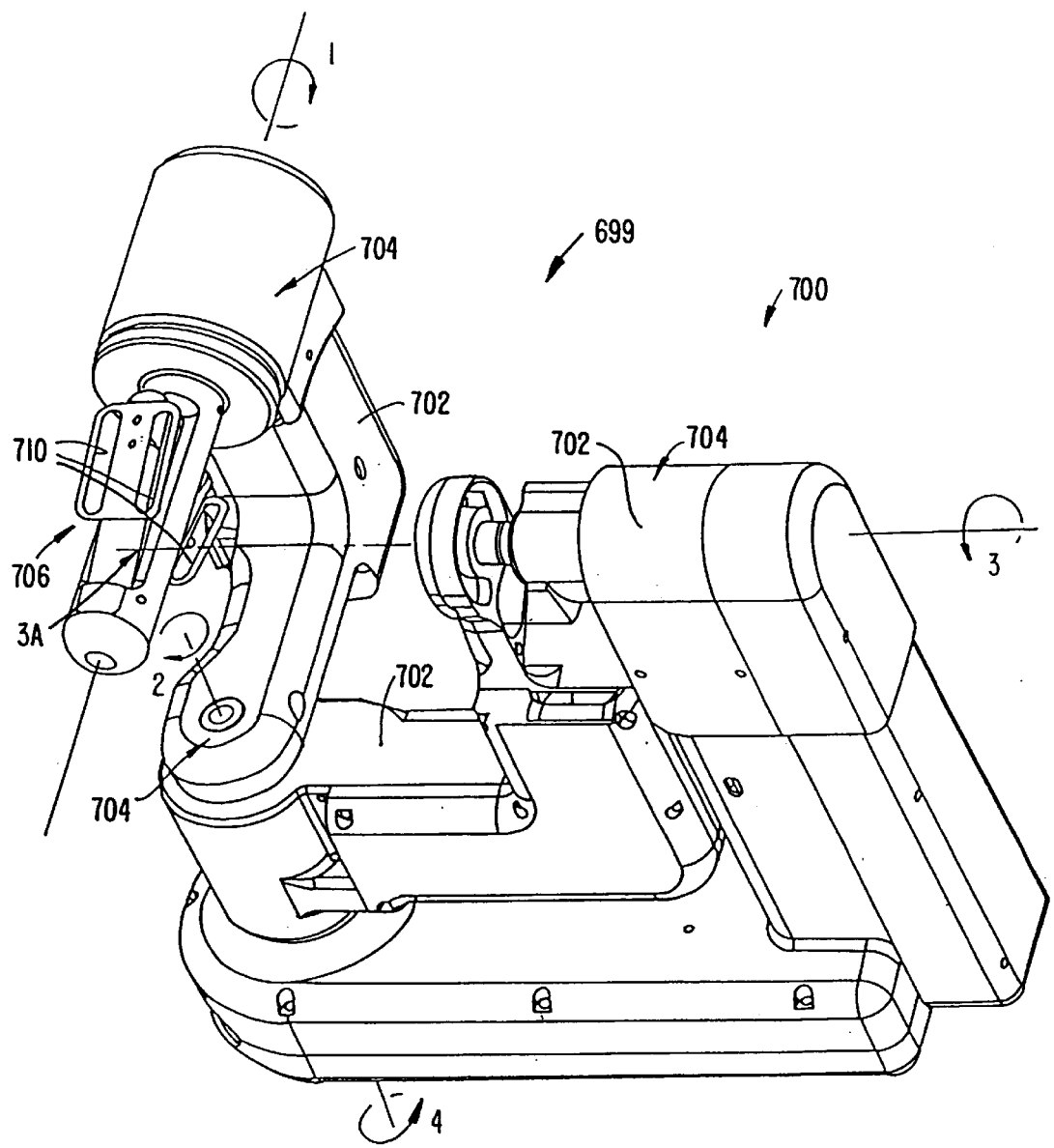
FIG. 6A shows a three-dimensional view of a hand held part or wrist gimbal of a master control device of the telesurgical system.
Figure 6B:
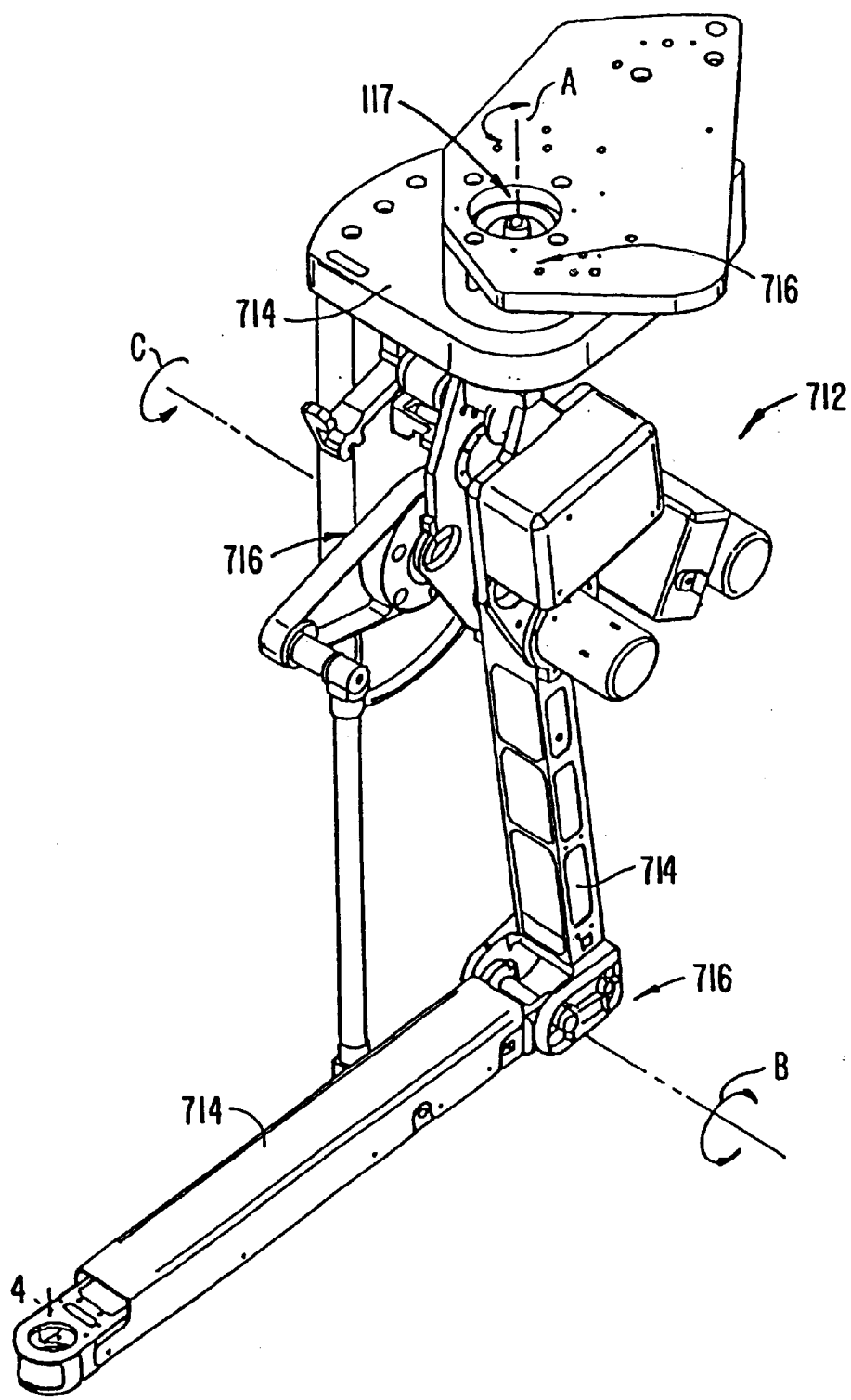
FIG. 6B shows a three-dimensional view of an articulated arm portion of the master control device of the telesurgical system on which the wrist gimbal of FIG. 6A is mounted in use.
Figure 6C:
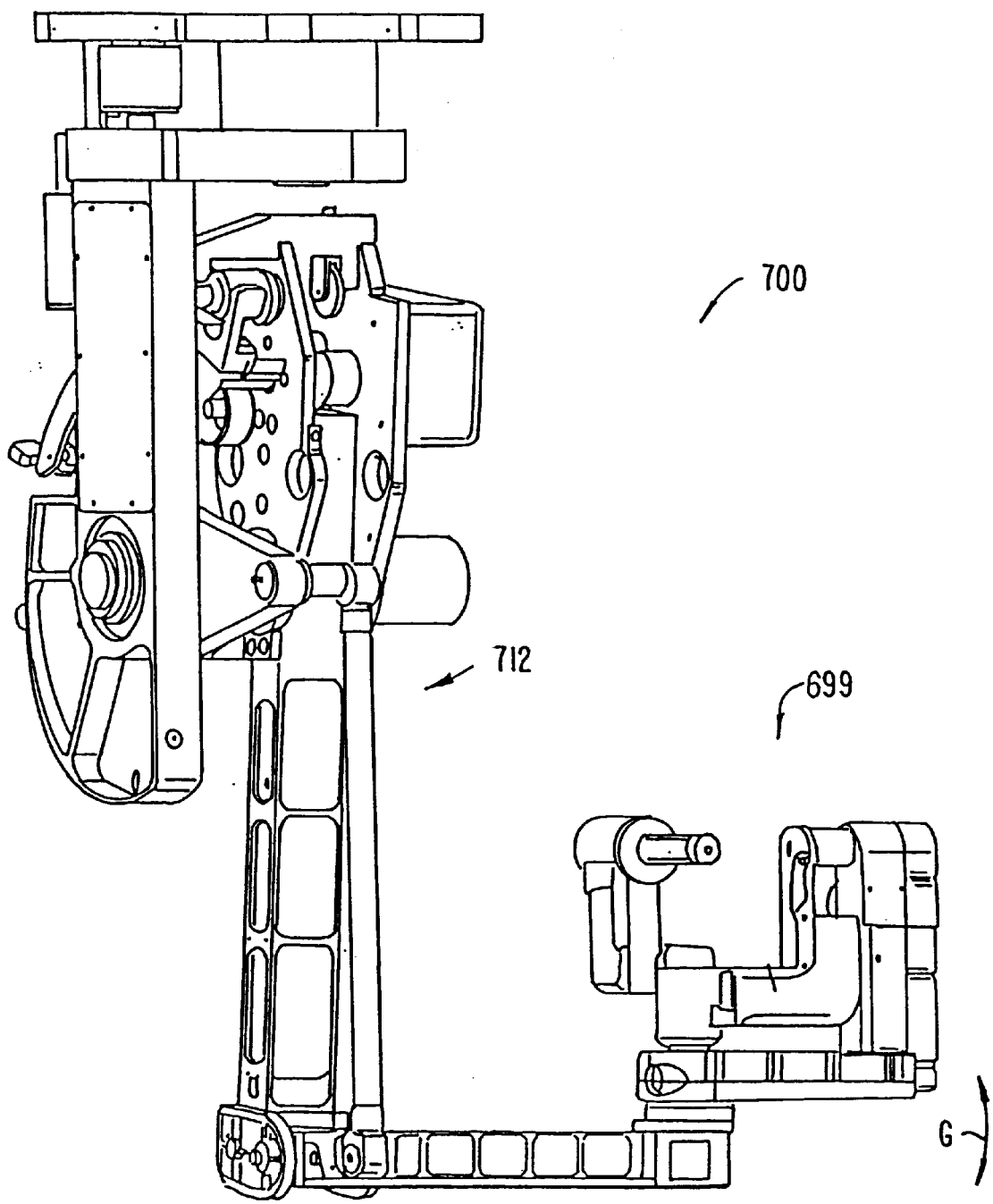
FIG. 6C shows a three-dimensional view of the master control device showing the wrist gimbal of FIG. 6A mounted on the articulated arm portion of FIG. 6B.

One of the master controls 700, 700 is indicated in FIG. 6C of the drawings. A hand held part or wrist gimbal of the master control device 700 is indicated in FIG. 6A and is generally indicated by reference numeral 699. Part 699 has an articulated arm portion including a plurality of members or links 702 connected together by pivotal connections or joints 704. The surgeon grips the part 699 by positioning his or her thumb and index finger over a pincher formation 706. The surgeon's thumb and index finger are typically held on the pincher formation 706 by straps (not shown) threaded through slots 710. When the pincher formation 706 is squeezed between the thumb and index finger, the fingers or end effector elements of the end effector 58 close. When the thumb and index finger are moved apart the fingers of the end effector 58 move apart in sympathy with the moving apart of the pincher formation 706. The joints of the part 699 are operatively connected to actuators, e.g., electric motors, or the like, to provide for, e.g., force feedback, gravity compensation, and/or the like, as described in greater detail hereinbelow. Furthermore, appropriately positioned sensors, e.g., encoders, or potentiometers, or the like, are positioned on each joint 704 of the part 699, so as to enable joint positions of the part 699 to be determined by the control system.

The part 699 is typically mounted on an articulated arm 712 as indicated in FIG. 6B. Reference numeral 4 in FIGS. 6A and 6B indicates the positions at which the part 699 and the articulated arm 712 are connected together. When connected together, the part 699 can displace angularly about an axis at 4.

The articulated arm 712 includes a plurality of links 714 connected together at pivotal connections or joints 716. It will be appreciated that also the articulated arm 712 has appropriately positioned actuators, e.g., electric motors, or the like, to provide for, e.g., force feedback, gravity compensation, and/or the like. Furthermore, appropriately positioned sensors, e.g., encoders, or potentiometers, or the like, are positioned on the joints 716 so as to enable joint positions of the articulated arm 712 to be determined by the control system as described in greater detail hereinbelow.

To move the orientation of the end effector 58 and/or its position along a translational path, the surgeon simply moves the pincher formation 706 to cause the end effector 58 to move to where he wants the end effector 58 to be in the image viewed in the viewer 202. Thus, the end effector position and/or orientation is caused to follow that of the pincher formation 706.

The master control devices 700, 700 are typically mounted on the station 200 through pivotal connections at 717 as indicated in FIG. 6B. As mentioned hereinbefore, to manipulate each master control device 700, the surgeon positions his or her thumb and index finger over the pincher formation 706. The pincher formation 706 is positioned at a free end of the part 699 which in turn is mounted on a free end of the articulated arm portion 712.

The electric motors and sensors associated with the robotic arms 12 and the surgical instruments 14 mounted thereon, and the electric motors and sensors associated with the master control devices 700 are operatively linked in the control system. The control system typically includes at least one processor, typically a plurality of processors, for effecting control between master control device input and responsive robotic arm and surgical instrument output and for effecting control between robotic arm and surgical instrument input and responsive master control output in the case of, e.g., force feedback.

Figure 7:
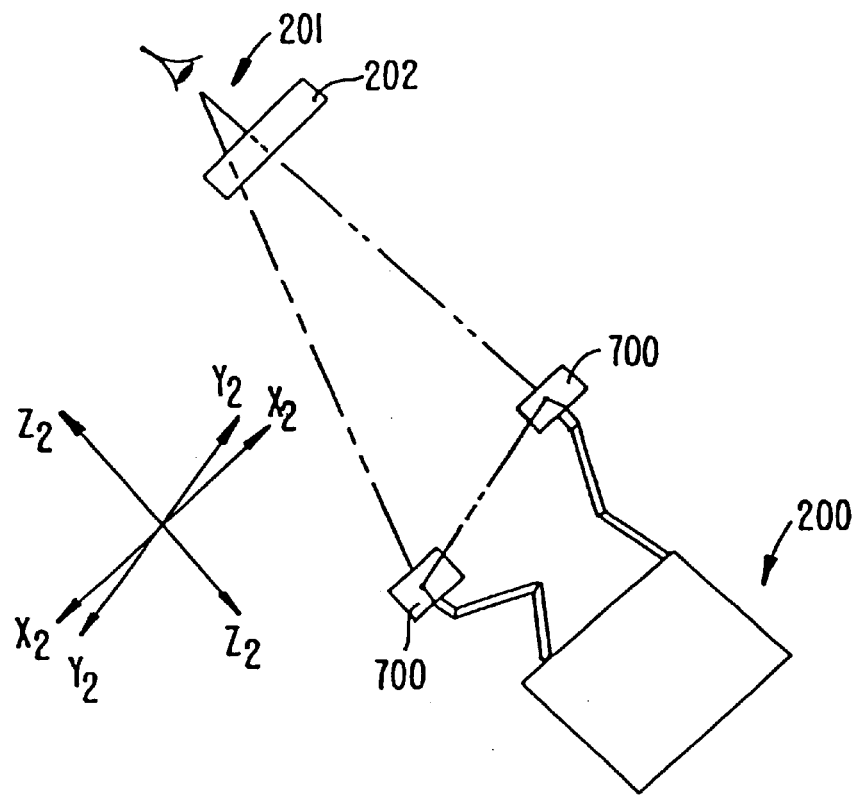
FIG. 7 shows a schematic three-dimensional drawing indicating the positions of the end effectors relative to a viewing end of an endoscope and the corresponding positions of master control devices relative to the eyes of an operator, typically a surgeon.
Figure 7:
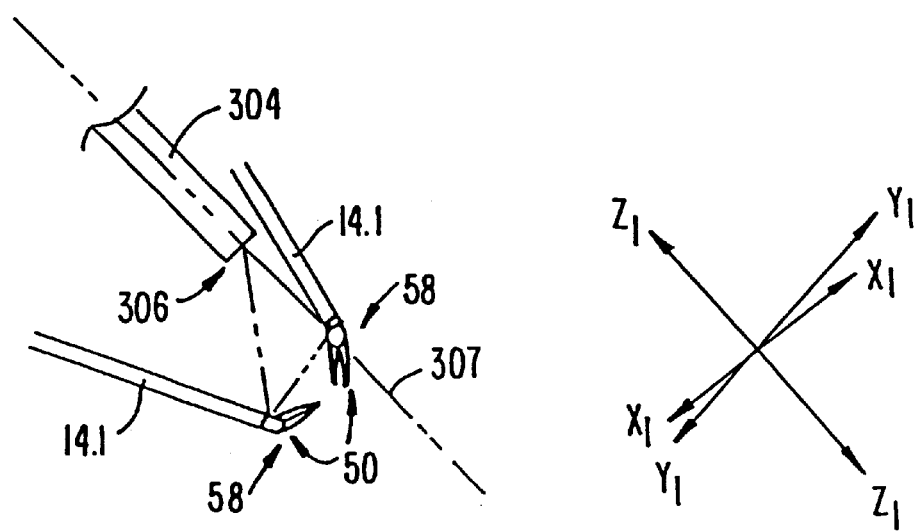

In use, and as schematically indicated in FIG. 7 of the drawings, the surgeon views the surgical site through the viewer 202. The end effector 58 carried on each arm 12 is caused to perform positional and orientational movements in response to movement and action inputs on its associated master controls. The master controls are indicated schematically at 700, 700. It will be appreciated that during a surgical procedure images of the end effectors 58 are captured by the endoscope 304 together with the surgical site and are displayed on the viewer 202 so that the surgeon sees the responsive movements and actions of the end effectors 58 as he or she controls such movements and actions by means of the master control devices 700, 700. The control system is arranged to cause end effector orientational and positional movement as viewed in the image at the viewer 202 to be mapped onto orientational and positional movement of a pincher formation of the master control as will be described in greater detail hereinbelow.

The operation of the control system of the minimally invasive surgical apparatus will now be described in greater detail. In the description which follows, the control system will be described with reference to a single master control 700 and its associated robotic arm 12 and surgical instrument 14. The master control 700 will be referred to simply as "master" and its associated robotic arm 12 and surgical instrument 14 will be referred to simply as "slave."

Figure 8:
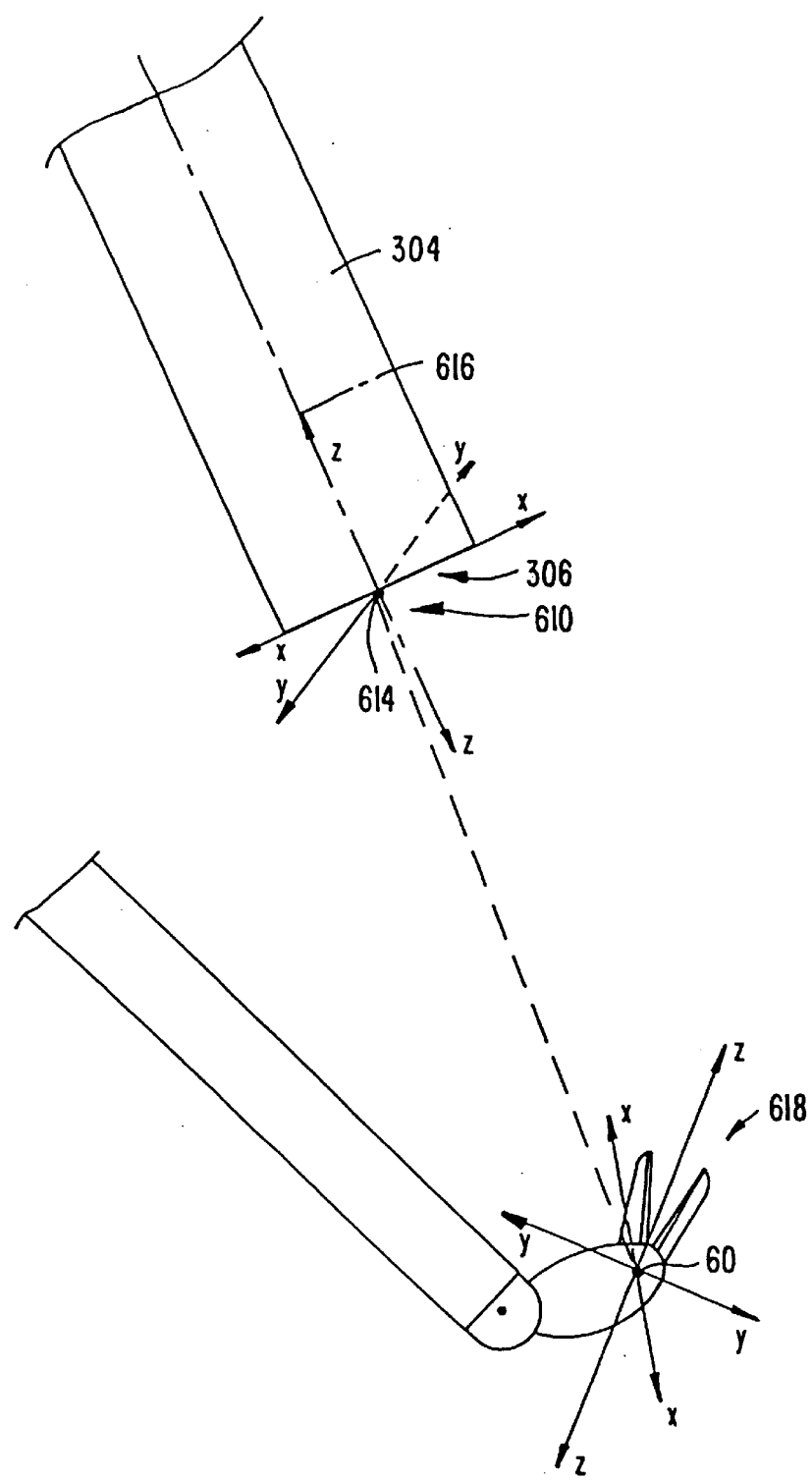
FIG. 8 shows a schematic three-dimensional drawing indicating the position and orientation of an end effector relative to a camera Cartesian coordinate reference system.

The method whereby control between master movement and corresponding slave movement is achieved by the control system of the minimally invasive surgical apparatus will now be described with reference to FIGS. 7 to 9 of the drawings in overview fashion. The method will then be described in greater detail with reference to FIGS. 10 to 21 of the drawings.

In essence, control between master and slave movement is achieved by comparing master position and orientation in an eye Cartesian coordinate reference system with slave position and orientation in a camera Cartesian coordinate reference system. For ease of understanding and economy of words, the term "Cartesian coordinate reference system" will simply be referred to as "frame" in the rest of this specification. Accordingly, when the master is stationary, the slave position and orientation within the camera frame is compared with the master position and orientation in the eye frame, and should the position and/or orientation of the slave in the camera frame not correspond with the position and/or orientation of the master in the eye frame, the slave is caused to move to a position and/or orientation in the camera frame at which its position and/or orientation in the camera frame does correspond with the position and/or orientation of the master in the eye frame. In FIG. 8, the camera frame is generally indicated by reference numeral 610 and the eye frame is generally indicated by reference numeral 612 in FIG. 9.

When the master is moved into a new position and/or orientation in the eye frame 612, the new master position and/or orientation does not correspond with the previously corresponding slave position and/or orientation in the camera frame 610. The control system then causes the slave to move into a new position and/or orientation in the camera frame 610 at which new position and/or orientation, its position and orientation in the camera frame 610 does correspond with the new position and/or orientation of the master in the eye frame 612.

It will be appreciated that the control system includes at least one, and typically a plurality, of processors which compute new corresponding positions and orientations of the slave in response to master movement input commands on a continual basis determined by the processing cycle rate of the control system. A typical processing cycle rate of the control system under discussion is about 1300 Hz. Thus, when the master is moved from one position to a next position, the corresponding movement required by the slave to respond is computed at about 1300 Hz. Naturally, the control system can have any appropriate processing cycle rate depending on the processor or processors used in the control system.

The camera frame 610 is positioned such that its origin 614 is positioned at the viewing end 306 of the endoscope 304. Conveniently, the z axis of the camera frame 610 extends axially along a viewing axis 616 of the endoscope 304. Although in FIG. 8, the viewing axis 616 is shown in coaxial alignment with a shaft axis of the endoscope 304, it is to be appreciated that the viewing axis 616 can be angled relative thereto. Thus, the endoscope can be in the form of an angled scope. Naturally, the x and y axes are positioned in a plane perpendicular to the z axis. The endoscope is typically angularly displaceable about its shaft axis. The x, y and z axes are fixed relative to the viewing axis of the endoscope 304 so as to displace angularly about the shaft axis in sympathy with angular displacement of the endoscope 304 about its shaft axis.

To enable the control system to determine slave position and orientation, a frame is defined on or attached to the end effector 58. This frame is referred to as an end effector frame or slave tip frame, in the rest of this specification, and is generally indicated by reference numeral 618. The end effector frame 618 has its origin at the pivotal connection 60. Conveniently, one of the axes e.g. the z axis, of the frame 618 is defined to extend along an axis of symmetry, or the like, of the end effector 58. Naturally, the x and y axes then extend perpendicularly to the z axis. It will appreciated that the orientation of the slave is then defined by the orientation of the frame 618 having its origin at the pivotal connection 60, relative to the camera frame 610. Similarly, the position of the slave is then defined by the position of the origin of the frame at 60 relative to the camera frame 610.

Figure 9:
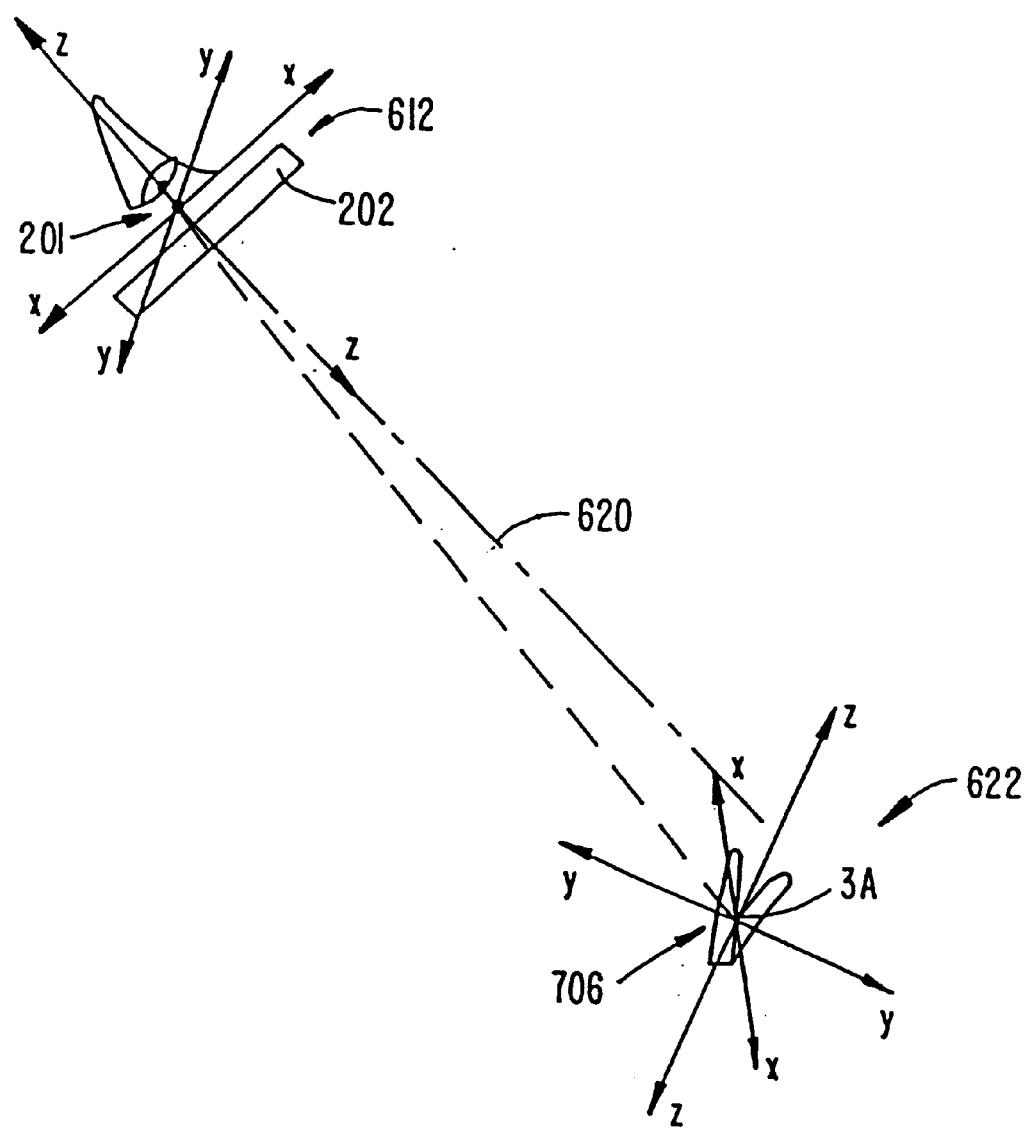
FIG. 9 shows a schematic three-dimensional drawing indicating the position and orientation of a pincher formation of the master control device relative to an eye Cartesian coordinate reference system.

Referring now to FIG. 9 of the drawings, the eye frame 612 is chosen such that its origin corresponds with a position 201 where the surgeon's eyes are normally located when he or she is viewing the surgical site at the viewer 202. The z axis extends along a line of sight of the surgeon, indicated by axis 620, when viewing the surgical site through the viewer 202. Naturally, the x and y axes extend perpendicularly from the z axis at the origin 201. Conveniently, the y axis is chosen to extend generally vertically relative to the viewer 202 and the x axis is chosen to extend generally horizontally relative to the viewer 202.

To enable the control system to determine master position and orientation within the viewer frame 612, a point on the master is chosen which defines an origin of a master or master tip frame, indicated by reference numeral 622. This point is chosen at a point of intersection indicated by reference numeral 3A between axes of rotation 1 and 3 of the master, as can best be seen in FIG. 6A of the drawings. Conveniently, the z axis of the master frame 622 on the master extends along an axis of symmetry of the pincher formation 706 which extends coaxially along the rotational axis 1. The x and y axes then extend perpendicularly from the axis of symmetry 1 at the origin 3A. Accordingly, orientation of the master within the eye frame 612 is defined by the orientation of the master frame 622 relative to the eye frame 612. The position of the master in the eye frame 612 is defined by the position of the origin 3A relative to the eye frame 612.

Figure 10:
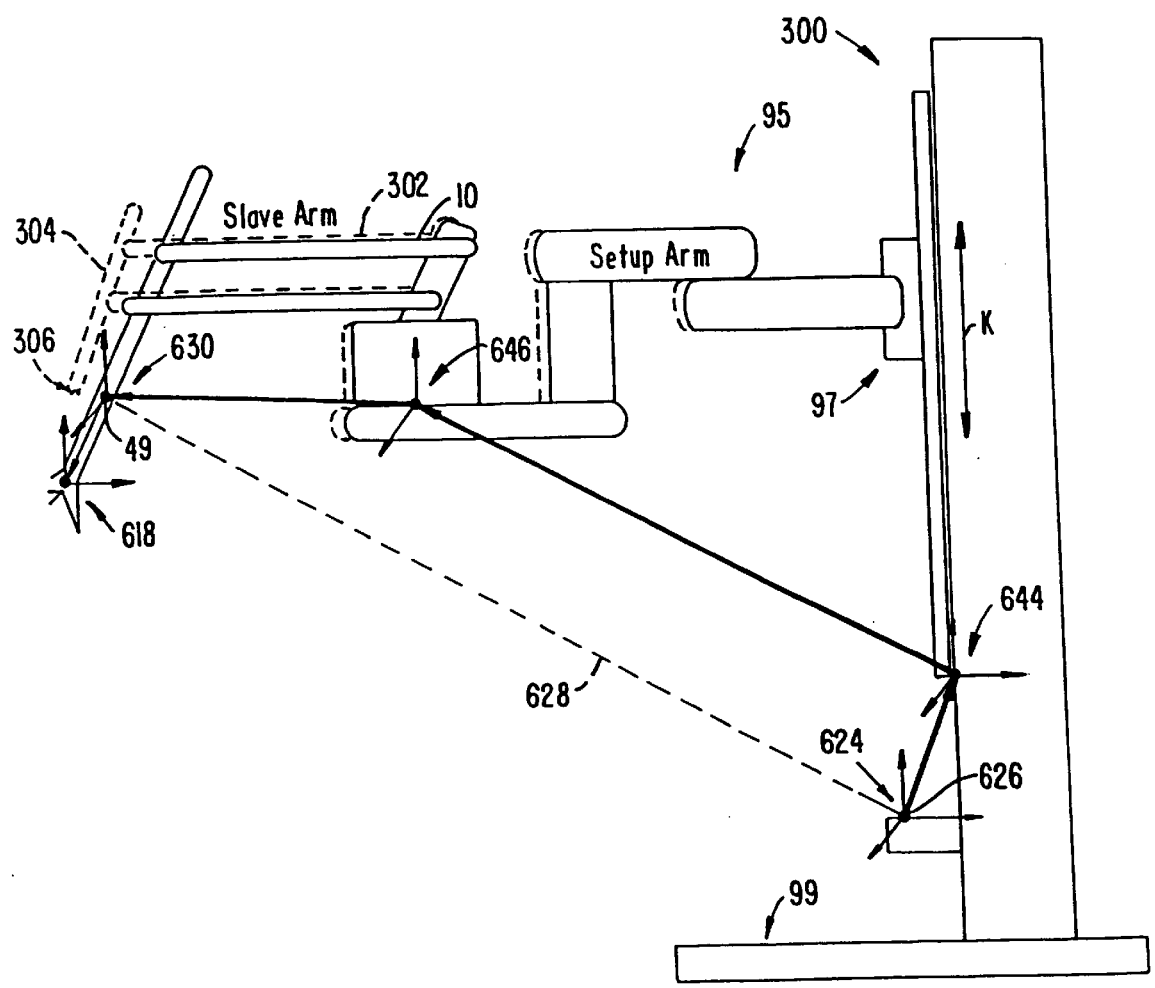
FIG. 10 shows a schematic side view of part of the surgical station of the minimally invasive surgical apparatus indicating the location of Cartesian reference coordinate systems used by a control system of the minimally invasive surgical apparatus to determine the position and orientation of an end effector relative to a Cartesian reference coordinate system at the viewing end of an image capturing device.

How the position and orientation of the slave within the camera frame 610 is determined by the control system will now be described with reference to FIG. 10 of the drawings. FIG. 10 shows a schematic diagram of one of the robotic arm 12 and surgical instrument 14 assemblies mounted on the cart 300. However, before commencing with a description of FIG. 10, it is appropriate to describe certain previously mentioned aspects of the surgical station 300 which impact on the determination of the orientation and position of the slave relative to the camera frame 610.

In use, when it is desired to perform a surgical procedure by means of the minimally invasive surgical apparatus, the surgical station 300 is moved into close proximity to a patient requiring the surgical procedure. The patient is normally supported on a surface such as an operating table, or the like. To make allowance for support surfaces of varying height, and to make allowance for different positions of the surgical station 300 relative to the surgical site at which the surgical procedure is to be performed, the surgical station 300 is provided with the ability to have varying initial setup configurations. Accordingly, the robotic arms 12, 12, and the endoscope arm 302 are mounted on the carriage 97 which is heightwise adjustable, as indicated by arrows K, relative to the base 99 of the cart 300, as can best be seen in FIGS. 1B and 10 of the drawings. Furthermore, the robotic arms 12, 12 and the endoscope arm 302 are mounted on the carriage 97 by means of the setup joint arms 95. Thus, the lateral position and orientation of the arms 12, 12, 302 can be selected by moving the setup joint arms 95. Thus, at the commencement of the surgical procedure, the cart 300 is moved into the position in close proximity to the patient, an appropriate height of the carriage 97 is selected by moving it to an appropriate height relative to the base 99 and the surgical instruments 14 are moved relative to the carriage 97 so as to introduce the shafts of the instruments 14 and the endoscope 304 through the ports of entry and into positions in which the end effectors 58 and the viewing end 306 of the endoscope 304 are appropriately positioned at the surgical site and the fulcrums are coincident with the ports of entry. Once the height and positions are selected, the carriage 97 is locked at its appropriate height and the setup joint arms 95 are locked in their positions and orientations. Normally, throughout the surgical procedure, the carriage 97 is maintained at the selected height and similarly the setup joint arms 95 are maintained in their selected positions. However, if required, either the endoscope or one or both of the instruments can be introduced through other ports of entry during the surgical procedure.

Returning now to FIG. 10, the determination by the control system of the position and orientation of the slave within the camera frame 610 will now be described. It will be appreciated that this is achieved by means of one or more processors having a specific processing cycle rate. Thus, where appropriate, whenever position and orientation are referred to in this specification, it should be borne in mind that a corresponding velocity is also readily determined. The control system determines the position and orientation of the slave within the camera frame 610 by determining the position and orientation of the slave relative to a cart frame 624 and by determining the orientation and position of the endoscope 304 with reference to the same cart frame 624. The cart frame 624 has an origin indicated by reference numeral 626 in FIG. 10.

To determine the position and orientation of the slave relative to the cart frame 624, the position of a fulcrum frame 630 having its origin at the fulcrum 49 is determined within the cart frame 624 as indicated by the arrow 628 in dashed lines. It will be appreciated that the position of the fulcrum 49 normally remains at the same location, coincident with a port of entry into the surgical site, throughout the surgical procedure. The position of the end effector frame 618 on the slave, having its origin at the pivotal connection 60, is then determined relative to the fulcrum frame 630 and the orientation of the end effector frame 618 on the slave is also determined relative to the fulcrum frame 630. The position and orientation of the end effector frame 618 relative to the cart frame is then determined by means of routine calculation using trigonometric relationships.

It will be appreciated that the robotic arm 302 of the endoscope 304 is constrained to move in similar fashion to the robotic arm 10, as indicated schematically in FIG. 4 of the drawings. Thus, the endoscope 304 when positioned with its viewing end 306 directed at the surgical site, also defines a fulcrum coincident with its associated port of entry into the surgical site. The endoscope arm 302 can be driven to cause the endoscope 304 to move into a different position during a surgical procedure, to enable the surgeon to view the surgical site from a different position in the course of performing the surgical procedure. It will be appreciated that movement of the viewing end 306 of the endoscope 304 is performed by varying the orientation of the endoscope 304 relative to its pivot center or fulcrum. The position and orientation of the camera frame 610 within the cart frame 624 is determined in similar fashion to the position and orientation of the slave within the cart frame 624. When the position and orientation of the camera frame 610 relative to the cart frame 624, and the position and orientation of the slave relative to the cart frame 624 have been determined in this manner, the position and the orientation of the slave relative to the camera frame 610 is readily determinable through routine calculation using trigonometric relationships.

Figure 11:
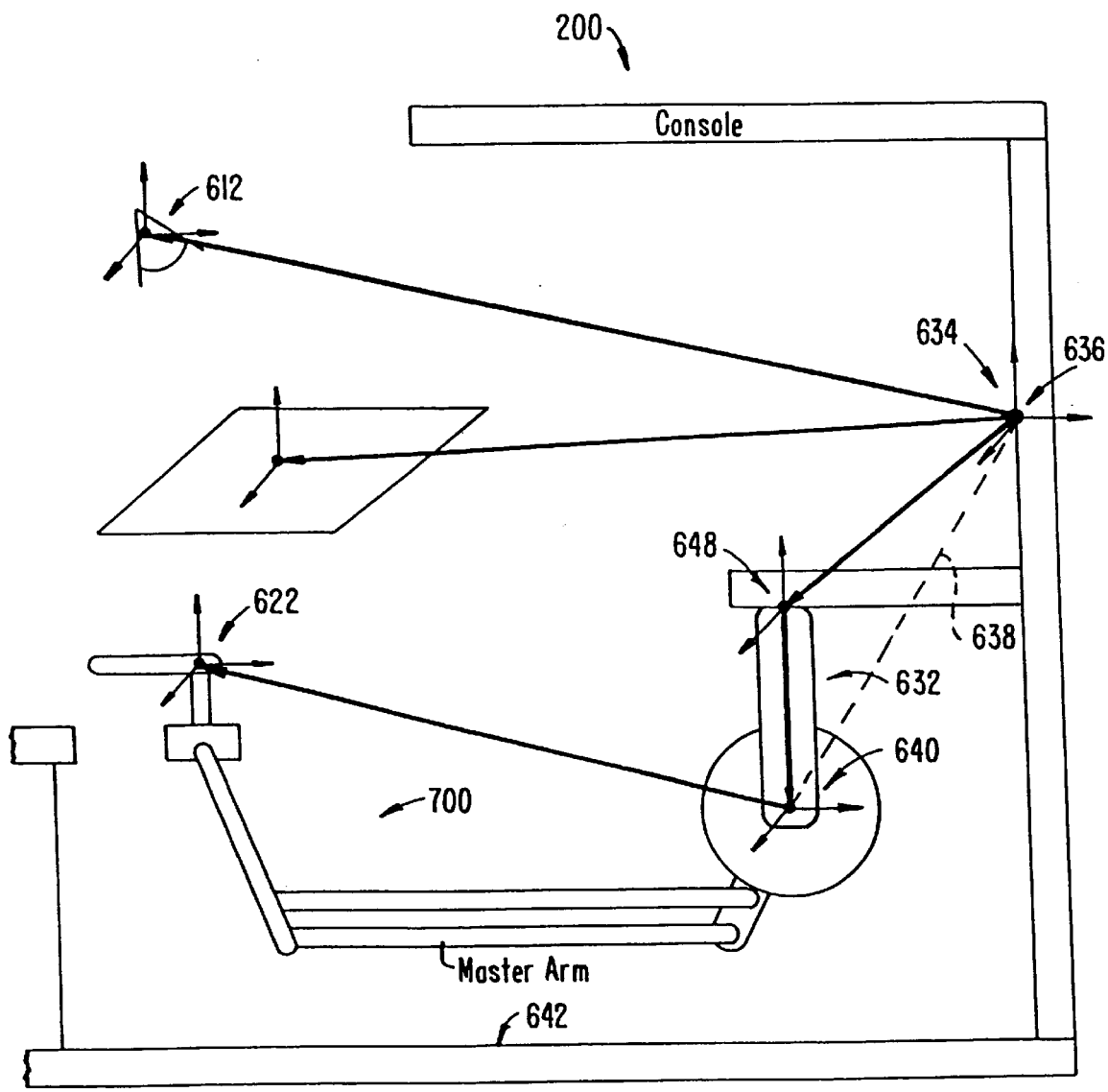
FIG. 11 shows a schematic side view of part of the operator station of the minimally invasive surgical apparatus indicating the location of Cartesian reference coordinate systems used by the control system of the minimally invasive surgical apparatus to determine the position and orientation of the pincher formation of the master control device relative to an eye Cartesian reference coordinate system.

How the position and orientation of the master within the viewer frame 612 is determined by the control system will now be described with reference to FIG. 11 of the drawings. FIG. 11 shows a schematic diagram of one of the master controls 700 at the operator station 200.

The operator station 200 optionally also includes setup joint arms, as indicated at 632, to enable the general location of the masters 700, 700 to be varied to suit the surgeon. Thus, the general position of the masters 700, 700 can be selectively varied to bring the masters 700, 700 into a general position at which they are comfortably positioned for the surgeon. When the masters 700, 700 are thus comfortably positioned, the setup joint arms 632 are locked in position and are normally maintained in that position throughout the surgical procedure.

To determine the position and orientation of the master 700, as indicated in FIG. 11, within the eye frame 612, the position and orientation of the eye frame 612 relative to a surgeon's station frame 634, and the position and orientation of the master 700 relative to the surgeon's frame 634 is determined. The surgeon's station frame 634 has its origin at a location which is normally stationary during the surgical procedure, and is indicated at 636.

To determine the position and orientation of the master 700 relative to the station frame 634, a position of a master setup frame 640 at an end of the setup joint arms 632 on which the master 700 is mounted, relative to the station frame 636, is determined, as indicated by the arrow 638 in dashed lines. The position and orientation of the master frame 622 on the master 700 having its origin at 3A is then determined relative to the master setup frame 640. In this manner, the position and orientation of the master frame 622 relative to the frame 634 can be determined by means of routine calculation using trigonometric relationships. The position and orientation of the eye frame 612 relative to the station frame 634 is determined in similar fashion. It will be appreciated that the position of the viewer 202 relative to the rest of the surgeon's console 200 can selectively be varied to suit the surgeon. The position and orientation of the master frame 622 relative to the eye frame 612 can then be determined from the position and orientation of the master frame 622 and the eye frame 612 relative to the surgeon station frame 634 by means of routine calculation using trigonometric relationships.

In the manner described above, the control system of the minimally invasive surgical apparatus determines the position and orientation of the end effector 58 by means of the end effector frame 618 in the camera frame 610, and, likewise, determines the position and orientation of the master by means of the master frame 622 relative to the eye frame 612.

As mentioned, the surgeon grips the master by locating his or her thumb and index finger over the pincher formation 706. When the surgeon's thumb and index finger are located on the pincher formation, the point of intersection 3A is positioned inwardly of the thumb and index finger tips. The master frame having its origin at 3A is effectively mapped onto the end effector frame 618, having its origin at the pivotal connection 60 of the end effector 58 as viewed by the surgeon in the viewer 202. Thus, when performing the surgical procedure, and the surgeon manipulates the position and orientation of the pincher formation 706 to cause the position and orientation of the end effector 58 to follow, it appears to the surgeon that his or her thumb and index finger are mapped onto the fingers of the end effector 58 and that the pivotal connection 60 of the end effector 58 corresponds with a virtual pivot point of the surgeon's thumb and index finger inwardly from the tips of the thumb and index finger. It will be appreciated that depending upon the actual configuration of the pincher formation, in particular the point of intersection of the axes 1 and 3 relative to the position of the pincher formation 706, the frame 622 on the master 700 can be offset from the intersection 3A so as to approach a point relative to the surgeon's hand at which point the pivotal connection 60 approximately corresponds.

Accordingly, as the surgical procedure is being performed the position and orientation of the fingers of the end effector tracks orientation and position changes of the surgeon's thumb and index finger in a natural intuitive or superimposed fashion. Furthermore, actuation of the end effector 58, namely causing the end effector fingers selectively to open and close, corresponds intuitively to the opening and closing of the surgeon's thumb and index finger. Thus, actuation of the end effector 58 as viewed in the viewer 302 is performed by the surgeon in a natural intuitive manner, since the pivot point 60 of the end effector 58 is appropriately mapped onto a virtual pivot point between the surgeon's thumb and index finger.

It will be appreciated that the end effector frame 618 can, where appropriate, be offset relative to the pivotal connection 60. Thus, for example, should the end effector have fingers of a relatively long length, the origin of the end effector frame can be offset in a direction toward the end effector finger tips. It will also be appreciated that using positional and/or orientational offsets between the master frame 622 and the intersection 3A, as well as between the end effector frame 618 and the pivotal connection 60, the mapping of the pincher formation 706 onto the end effector 58 may be shifted, for example to map the tips of the pincher formation onto the tips of the end effector.

It will be appreciated that the cart frame 624 can be chosen at any convenient location in which its origin corresponds with a location on the cart 300 which does not vary relative to its base 99. The surgeon's station frame 634 can likewise be chosen at any convenient location such that its origin is located at a position which does not vary relative to a base 642 thereof. Furthermore, to determine the position and orientation of the camera frame 610 relative to the cart frame 624, use can be made of a plurality of different intermediate frame paths. To determine the position and orientation of the end effector frame 618 relative to the cart frame 624 use can also be made of a plurality of different intermediate frame paths.

However, it has been found that should the intermediate frame paths be appropriately selected, the control system is then arranged to be readily adaptable to accommodate modular replacement of modular parts having different characteristics than the modular parts being replaced. It will be appreciated that selecting intermediate frames also eases the computational process involved in determining master and slave position and orientation.

Referring again to FIG. 10 of the drawings, the cart frame is chosen at 624, as already mentioned. It will be appreciated that determining the position of the fulcrum frame 630 relative to the cart frame 624 is achieved through appropriately positioned sensors, such as potentiometers, encoders, or the like. Conveniently, the fulcrum frame position 630 relative to the cart frame 624 is determined through two intermediate frames. One of the frames is a carriage guide frame 644 which has its origin at a convenient location on a guide along which the carriage 97 is guided. The other frame, an arm platform frame indicated at 646 is positioned at an end of the setup joint arm 95 on which the robotic arm 12 is mounted. Thus, when slave position and orientation is determined relative to the cart frame 624, the carriage guide frame 644 position relative to the cart frame 624 is determined, then the platform frame 646 position relative to the carriage guide frame 644, then the fulcrum frame 630 relative to the platform frame 646, and then the slave orientation and position relative to the fulcrum frame 630, thereby to determine the slave position and orientation relative to the cart frame 624. It will be appreciated that the slave position and orientation relative to the cart frame 624 is determined in this manner for each arm 10 and in similar fashion for the camera frame 610, through its arm 302, relative to the cart frame 624.

Referring to FIG. 11, the position and orientation of the master control is determined by determining the position of a base frame 648 relative to the surgeon's station frame 634, then determining the position of the platform frame 640 relative to the base frame 648, and then determining master position and orientation relative to the platform frame 640. The position and orientation of the master frame 622 relative to the surgeon's station frame 634 is then readily determined through routine calculation using trigonometric relationships. It will be appreciated that the position and orientation of the other master frame relative to the surgeon console frame 634 is determined in a similar fashion.

Referring to FIG. 10, by choosing the frames as described, the setup joint 95 can be replaced with another setup joint while the same robotic arm is used. The control system can then be programmed with information, e.g., arm lengths and/or the like, relating to the new setup joint only. Similarly, the robotic arm 10 can be replaced with another arm, the control system then requiring programming with information, e.g., fulcrum position and/or the like, relating to the new robotic arm only. It will be appreciated that in this way the endoscope arm 302 and its associated setup joint can also be independently replaced, the control system then requiring programming of information relating only to the part being replaced. Furthermore, referring to FIG. 11, the setup joint and master control can also independently be replaced, the control system requiring programming of information relating to the characteristics of the new part only.

Further aspects of the control system of the minimally invasive surgical apparatus will now be described with reference to FIG. 12.

Figure 12:
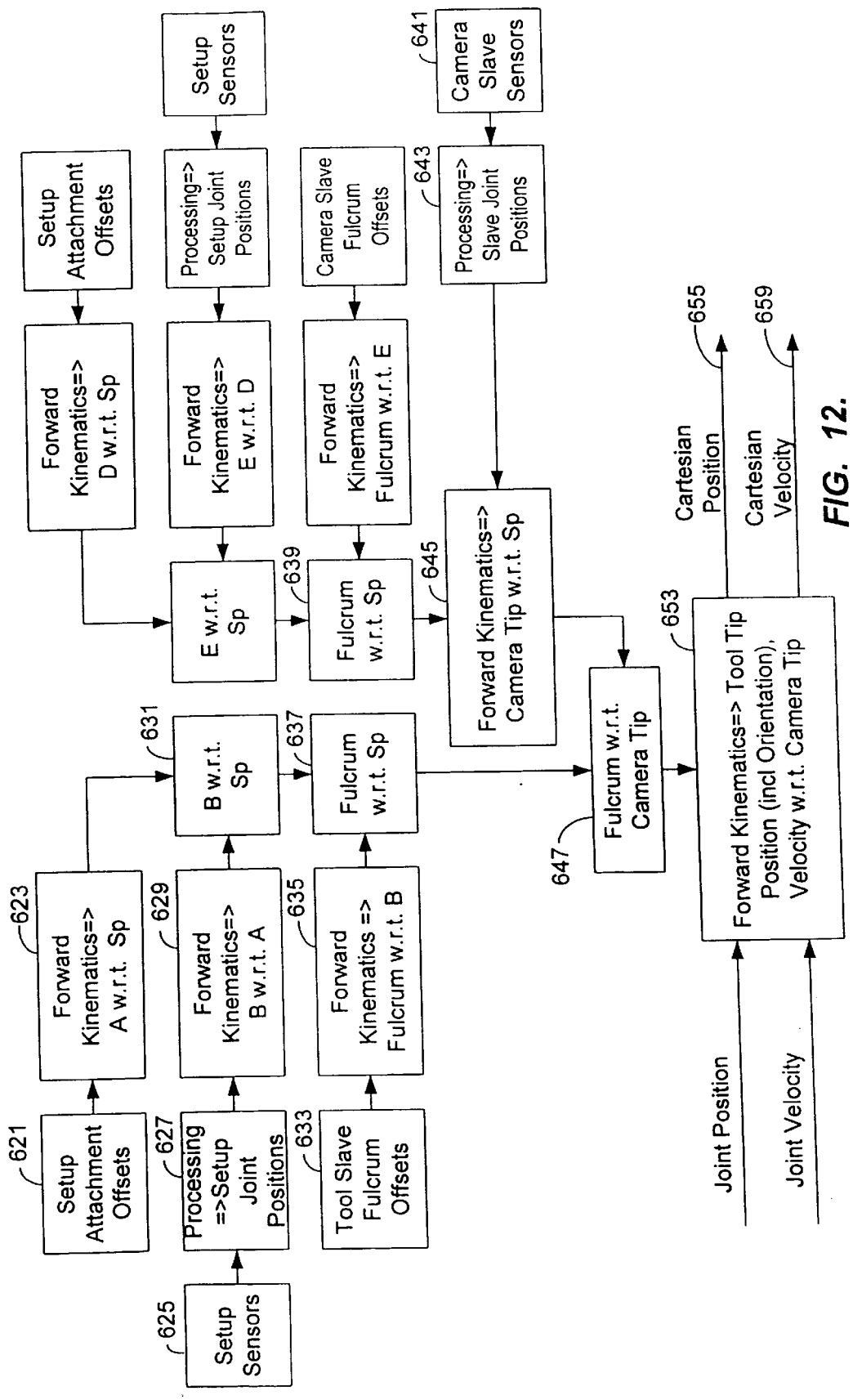
FIG. 12 shows a schematic block diagram indicating steps followed by the control system of the minimally invasive surgical apparatus in determining end effector position and orientation relative to the Cartesian reference coordinate system at the viewing end of the image capturing device.

FIG. 12 indicates the control steps whereby the control system of the minimally invasive surgical apparatus determines slave position and orientation, namely the position and orientation of the end effector frame 618 in the camera frame 610.

The position or offsets of the carriage guide frame 644 relative to the cart frame 624 is indicated at 621. The offsets at 621 are fed through a forward kinematics block (FKIN) at 623 to yield corresponding Cartesian coordinates of the frame 644 relative to the cart frame 624.

Sensors 625 operatively associated with the setup joint arm 95 and sensors determining the height of the carriage 97, are read by a processor 627 to determine translational and joint positions. The translational and joint positions are then input to an FKIN block 629 to determine corresponding Cartesian coordinates. At 631, the Cartesian coordinates of the carriage guide frame 644 relative to the cart frame 624 and the Cartesian coordinates of the platform frame 646 relative to the carriage frame 644 are used to determine the Cartesian coordinates of the platform frame 646 relative to the cart frame 624.

Since the position of the fulcrum 49 relative to the platform frame 646 does not change, an offset relative to the platform frame 646, indicated at 633, is input to an FKIN controller at 635 to yield Cartesian coordinates of the fulcrum frame 630 relative to the platform frame 646. It will be appreciated that, where appropriate, the term FKIN controller is to be interpreted to include an appropriate conversion matrix and kinematic relationships. At 637, the Cartesian coordinates of the fulcrum frame 630 relative to the cart frame 624 are determined by means of the values determined at 631 and 635 respectively.

It will be appreciated that, in similar fashion, the Cartesian coordinates of the fulcrum of the endoscope is determined relative to the cart frame 624. This is indicated at 639.

As mentioned, the position and orientation of the endoscope 304 can be varied. The position and orientation of the endoscope 304 can be varied during set up of the cart 300 before the surgical procedure commences or during the performance of a surgical procedure should the surgeon wish to view the surgical site from a different location.

To enable the control system to determine endoscope position and orientation relative to the cart frame 624, sensors are provided on its associated arm 302. These sensors, indicated at 641, are read by a processor at 643 to determine joint positions. The joint positions thus determined are fed to an FKIN controller at 645, together with the Cartesian coordinates determined at 639 to determine endoscope orientation and position relative to the cart frame 624. These values are then input to 647 together with the values determined at 637, so as to enable the fulcrum frame 630 of the slave to be determined relative to the camera frame 610.

During the course of the surgical procedure, the slave orientation and position is normally constantly changing. Varying joint positions and velocities are fed into an FKIN controller at 653, together with the Cartesian coordinate values of the slave position relative to the camera frame determined at 647 to yield Cartesian position and velocity of the slave, namely the end effector frame 618, relative to the camera frame 610, as indicated by arrows 655, 657 respectively. For economy of words, Cartesian position is to be interpreted to include Cartesian orientation in the rest of this specification where appropriate. The varying joint positions and velocities are fed into the FKIN block 653 from a simulation domain as described in greater detail hereinbelow.

Figure 13:
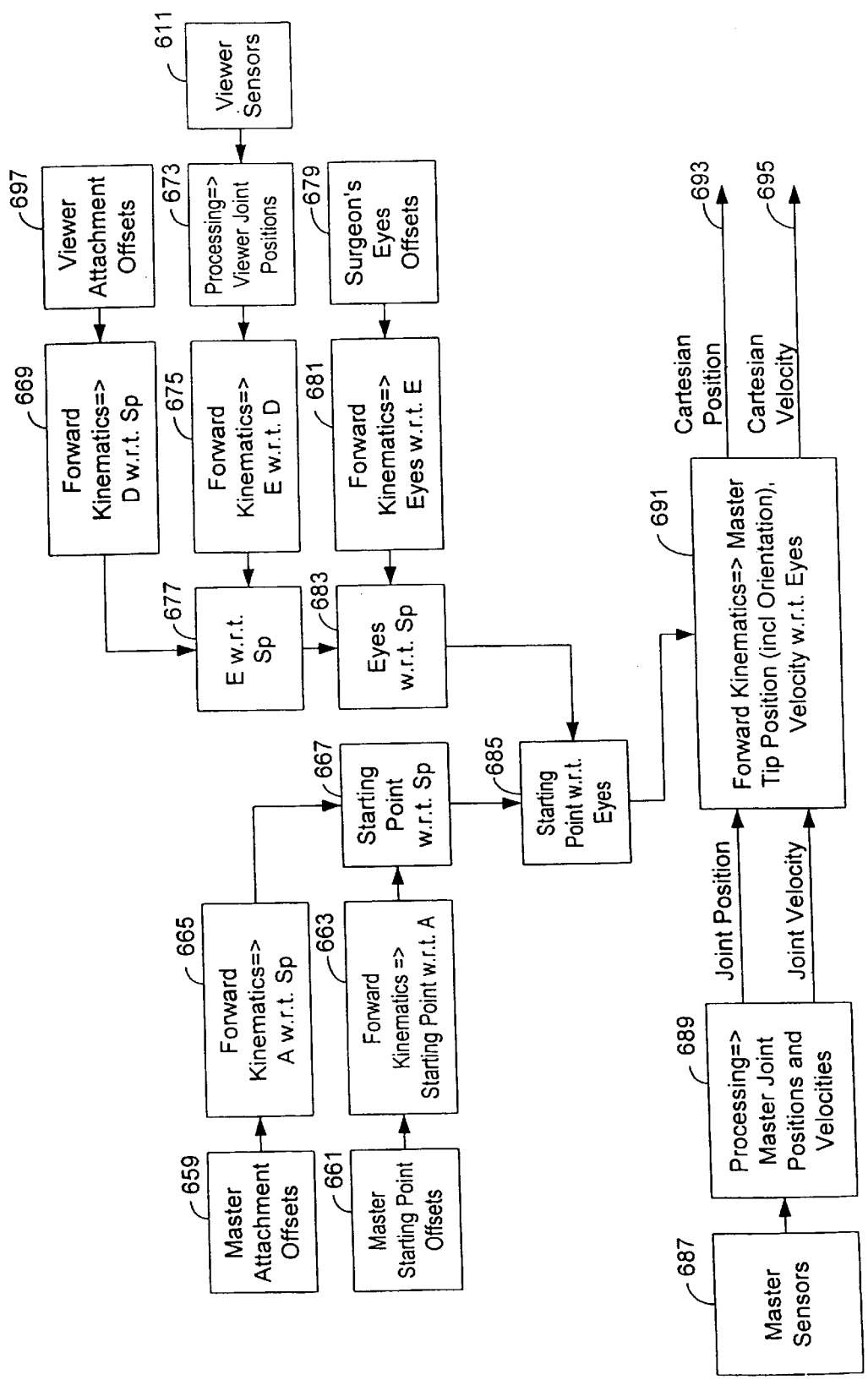
FIG. 13 shows a schematic block diagram indicating steps followed by the control system of the minimally invasive surgical apparatus in determining pincher formation position and orientation relative to the eye Cartesian reference coordinate system.

Referring now to FIG. 13, master position and orientation relative to the viewer frame 612 will now be described.

The base frame 648 normally does not change relative to the surgeon station frame 634. Similarly, the frame at 640 normally does not change relative to the base frame 648. As mentioned, setup joints can optionally be provided at 632 if required. For the sake of the description which follows, the position of the frame at 640 relative to the base frame 648 is assumed to be unchangeable. Naturally, if setup joint arms are provided at 632, appropriate sensors would then be provided to enable the position of the frame at 640 to be determined relative to the frame at 648.

Referring now to FIG. 13, offsets determining the frame 648 position relative to the surgeon station frame 634, as indicated at 659, are fed through an FKIN controller 665 to yield Cartesian coordinates of the base frame 648 relative to the surgeon station frame 634. Similarly, offsets relating to frame 640 position relative to base frame 648 position, as indicated at 661, are fed through an FKIN controller at 663 to yield Cartesian coordinates of the frame 640 relative to the base frame 648. From the values derived at 665, 663, the Cartesian coordinates of the frame 640 relative to the surgeon station frame 634 are determined at 667.

Offsets at 697 relating to a viewer base frame, not indicated in FIG. 11, are fed through an FKIN controller at 669 to yield corresponding Cartesian coordinates of the base frame relative to the frame 634. The viewer 202 can be positionally adjustable relative to the rest of the operator station 200. To enable a viewer position relative to the viewer base frame to be determined, appropriately positioned sensors 671 are provided. Sensor readings from these sensors at 671 are processed at 673 to determine joint or translational positions which are then fed through an FKIN controller at 675 to yield Cartesian coordinates of the viewer frame relative to the viewer base frame. At 677, the viewer frame position in Cartesian coordinates relative to the surgeon station frame 634 are determined from the values derived at 669 and 675 respectively.

Offsets corresponding to the position of the surgeon's eyes relative to the viewer frame at 679 are fed through an FKIN controller at 681 to yield Cartesian coordinates of the position of the surgeon's eyes relative to the viewer frame. At 683, the values from 677 and 681 are used to determine the surgeon's eye frame 612 relative to the surgeon station frame 634.

At 685, the values from 667 and 683 are used to determine the position of the frame 640 relative to the eye frame 612.

Naturally, master position and orientation relative to the eye frame 612 is continually changing during the course of a surgical procedure. The sensors on the master 700, indicated at 687, are read by a processor at 689 to determine master joint position and velocity. These joint position and velocity values are then fed through an FKIN controller at 691, together with the value derived at 685 to yield master Cartesian position and velocity values 693, 695 relating to Cartesian position and velocity of master frame 622, relative to the eye frame 612.

At the commencement of a surgical procedure, an initial position of the master 700 is set to correspond with an initial position of the slave. Thereafter, as the master 700 is moved, the control system monitors such movement and commands the slave to track the master movement. Thus, at the commencement of a surgical procedure, the frame 618 on the slave at the pivotal connection 60, relative to its reference frame 610 at the viewing end 306 of the endoscope 304, at the initial position, is mapped onto the master frame 622 relative to its reference eye frame 612 at its initial position. Similarly, the system maps an initial orientation of the pincher formation frame 622 with an initial orientation of the end effector frame 618. Thus, the orientation of the end effector frame 618 is also caused to track the orientation of the master frame 622. The position and orientation of the slave in the camera frame 610 need not correspond identically with the position and orientation of the master in the eye frame 612. Accordingly, offsets can be introduced relating to the orientation and the position of the end effector frame 618 relative to the camera frame 610 to define an arbitrary end effector frame position and orientation which corresponds to a master frame 622 position and orientation in the eye frame 612. It will be appreciated that the control system can readily determine the orientation and the position of the end effector frame 618 relative to the camera frame 610 at which it is to correspond with that of the master frame relative to the eye frame by means of the frames and offsets discussed above. Thus, even during the course of a surgical procedure, if the control between master and slave is interrupted and the endoscope is moved, or one or both of the surgical instruments are repositioned through different ports of entry, or the master positions are changed at the surgeon's console, or the like, re-mapping of slave relative to master in their respective camera and eye frames can readily be achieved by the control system.

Figure 13A:
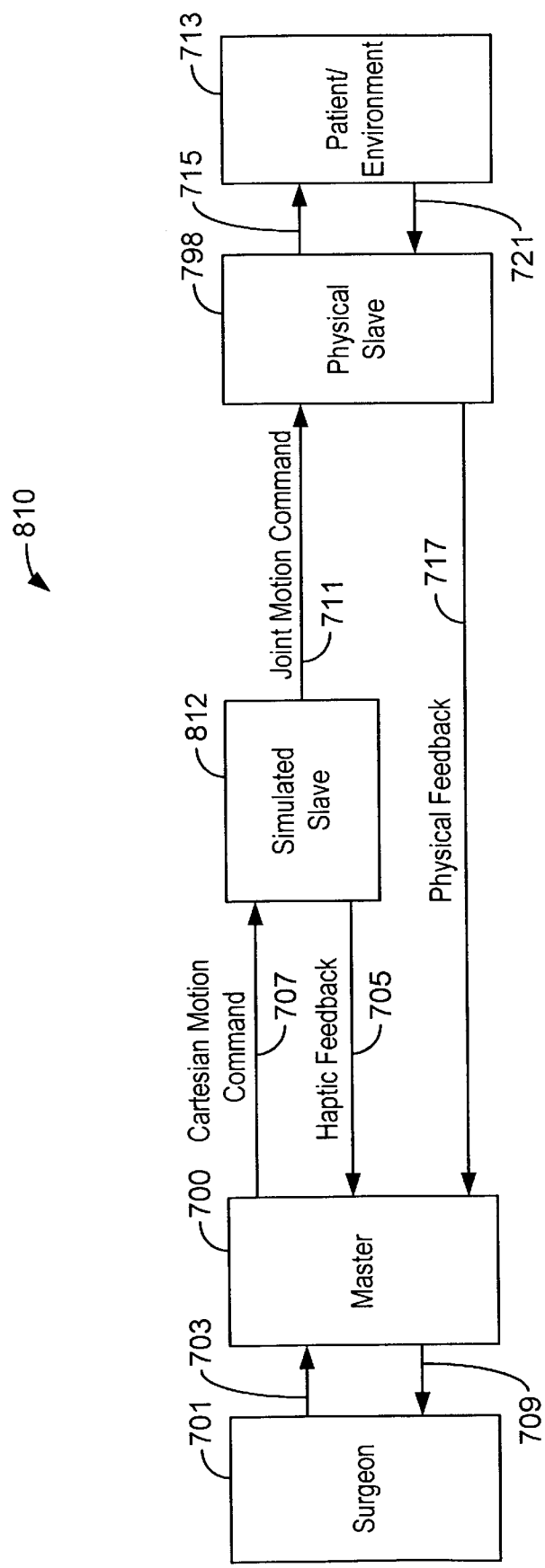
FIG. 13A shows an "overview" algorithm of a control system of a minimally invasive surgical apparatus in accordance with the invention.

The control system of the minimally invasive surgical apparatus will now be described in overview fashion with reference to FIG. 13A of the drawings and individual aspects of the control system will then be described in greater detail with reference to FIGS. 9 to 21. In FIG. 13A the control system of the minimally invasive surgical apparatus is generally indicated by reference numeral 810.

For ease of understanding and explanation, the control system 810 will be described in terms of the operative association between a single master control device and its associated robotic arm and instrument assembly. For economy of words, the master control device 700 will simply be referred to as master 700 in the rest of this specification. Similarly, its associated robotic arm and instrument assembly will simply be referred to as slave 798. The slave 798 includes one of the robotic arm assemblies 12 having a surgical instrument 14 mounted thereon.

Control between master 700 and slave 798 is performed by means of a simulated or virtual domain. The simulated domain is indicated by reference numeral 812.

The surgeon is schematically indicated at 701. The surgeon commands responsive slave movements by selectively moving the master 700 from one position to a next position on a continual basis during the performance of a surgical procedure. The movement input commands on the master 700 by the surgeon 701 is indicated by arrow 703.

The system 810 monitors the position of the master within a reference system as already described.

The movement input commands on the master 700 are transformed from joint space to Cartesian space and are then input to the simulated domain 812 as indicated by arrow 707. In the simulated domain 812 responsive slave movement commands as dictated by master input commands is continually monitored at the processing cycle rate, i.e., about 1300 Hz, of the control system 810. Thus, the simulated domain 812 monitors resultant slave responsive movement in a simulated environment before the actual slave 798 is instructed to respond to the master control input commands.

The slave 798 has certain physical movement limitations or constraints. For example, the end effector 58 cannot be moved to a position, relative to the mounting plate 16, beyond the positional range dictated by the mechanical arm and pivotal connection structures. Furthermore, it is desirable to limit to a maximum the velocity of the slave 798 when moving in response to master control input. Furthermore, the slave 798 has certain positional singularities, which will be described in greater detail hereinbelow, in which responsive movement is not readily achievable, and the closer a singularity is approached the more difficult it becomes for the slave 798 to respond effectively.

These limitations are imposed on the responsive slave movement commands in the simulated domain 812 before the actual slave 798 is instructed to respond. Thus, in the simulated domain 812, the control system tracks the simulated responsive slave movements. Should the responsive slave movements as dictated by master input commands not transgress these limitations, corresponding commands are sent to the actual slave 798 to cause it to track master movement input commands. However, should the master input commands correspond with a responsive slave movement in the simulated domain 812 which transgresses one or more of the limitations, the corresponding slave movement commands are restricted in the simulated domain 812 to remain within the limitations. Instructions corresponding to the restricted slave movement commands are then forwarded to the actual slave ensuring that the actual slave does not transgress the limitations set in the simulated domain 812. The instructions from the simulated domain 812 to the slave 798 are indicated by reference numeral 711 and are in the form of joint space commands. Where the slave movement commands have been restricted, instructions are sent to the master 700 corresponding to the degree of restriction and as indicated by arrow 705. In this manner, corresponding haptic feedback is provided on the master 700 so that the surgeon is urged not to move the master 700 in a manner causing the corresponding slave movement to transgress the set limitations.

Accordingly, the effect of the control system 810 is that where one or more limitations have been imposed on the slave commands, the actual slave 798 is prevented from transgressing the set limitations and at generally the same time the master 700 is caused to resist movement by the surgeon beyond such limitations. The resistance on the master 700 is typically caused by torques on the motors associated therewith. In this manner haptic feedback is supplied to the master which is felt by the surgeon as indicated by arrow 709.

As the slave 798 is caused to move in sympathy with master input commands, the end effector 58, interacts with the surgical site, indicated by reference numeral 713, as indicated by arrow 715.

The control system 810 also provides for actual feedback from the slave 798 to the master 700. Thus, should the actual slave 798 be subjected to an extraneous force, as indicated by arrow 721, physical feedback is directly supplied to the master 700 as indicated by arrow 717 and as discussed in greater detail hereinbelow. It will be appreciated that an extraneous force can typically be imposed on the slave 798 when the end effector 58 contacts tissue at the surgical site 713 for example.

The control system, generally indicated by reference numeral 810, will now be described in greater detail with reference to FIG. 14 of the drawings, in which like reference numerals are used to designate similar parts or aspects, unless otherwise stated.

As mentioned earlier, the master control 700 has sensors, e.g., encoders, or potentiometers, or the like, associated therewith to enable the control system 810 to determine the position of the master control 700 in joint space as it is moved from one position to a next position on a continual basis during the course of performing a surgical procedure. In FIG. 14, signals from these positional sensors are indicated by arrow 814. Positional readings measured by the sensors at 687 are read by the processor indicated at 689 (refer to FIG. 13). It will be appreciated that since the master control 700 includes a plurality of joints connecting one arm member thereof to the next, sufficient positional sensors are provided on the master 700 to enable the angular position of each arm member relative to the arm member to which it is joined to be determined thereby to enable the position and orientation of the master frame 622 on the master to be determined. As the angular positions of one arm member relative to the arm member to which it is joined is read cyclically by the processor 689 in response to movements induced on the master control 700 by the surgeon, the angular positions are continuously changing. The processor at 689 reads these angular positions and computes the rate at which these angular positions are changing. Thus, the processor 689 reads angular positions and computes the rate of angular change, or joint velocity, on a continual basis corresponding to the system processing cycle time, i.e., 1300 Hz. Joint position and joint velocity commands thus computed at 689 are then input to the Forward Kinematics (FKIN) controller at 691, as already described hereinabove.

At the FKIN controller 691, the positions and velocities in joint space are transformed into corresponding positions and velocities in Cartesian space, relative to the eye frame 612 (refer to FIGS. 11 and 13). The FKIN controller 691 is a processor which typically employs a Jacobian (J) matrix to accomplish this. It will be appreciated that the Jacobian matrix transforms angular positions and velocities into corresponding positions and velocities in Cartesian space by means of conventional trigonometric relationships. Thus, corresponding positions and velocities in Cartesian space, or Cartesian velocity and position commands, are computed by the FKIN controller 691 which correspond to Cartesian position and velocity changes of the master frame 622 in the eye frame 612.

The velocity and the position in Cartesian space is input into a Cartesian controller, indicated at 820, and into a scale and offset converter, indicated at 822.

The minimally invasive surgical apparatus provides for a scale change between master control input movement and responsive slave output movement. Thus, a scale can be selected where, for example, a 1-inch movement of the master control 700 is transformed into a corresponding responsive ⅕-inch movement on the slave. At the scale and offset step 822, the Cartesian position and velocity values are scaled in accordance with the scale selected to perform the surgical procedure. Naturally, if a scale of 1:1 has been selected, no change in scale is effected at 822. Similarly, offsets are taken into account which determine the corresponding position and/or orientation of the end effector frame 618 in the camera frame 610 relative to the position and orientation of the master frame 622 in the eye frame 612.

After a scale and offset step is performed at 822, a resultant desired slave position and desired slave velocity in Cartesian space is input to a simulated or virtual domain at 812, as indicated by arrows 811. It will be appreciated that the labeling of the block 812 as a simulated or virtual domain is for identification only. Accordingly, the simulated control described hereinbelow is performed by elements outside the block 812 also.

The simulated domain 812 will be described in greater detail hereinbelow. However, the steps imposed on the desired slave velocity and position in the virtual domain 812 will now be described broadly for ease of understanding of the description which follows. In essence, a current slave position and velocity is continually monitored in the virtual or simulated domain 812. The desired slave position and velocity is compared with the current slave position and velocity. Should the desired slave position and/or velocity as input from 822 not cause transgression of limitations, e.g., velocity and/or position and/or singularity, and/or the like, as set in the virtual domain 812, a similar Cartesian slave velocity and position is output from the virtual domain 812 and input into an inverse scale and offset converter as indicated at 826. The similar velocity and position output in Cartesian space from the virtual domain 812 is indicated by arrows 813 and corresponds with actual commands in joint space output from the virtual domain 812 as indicated by arrows 815 as will be described in greater detail hereinbelow. From the inverse scale and offset converter 826, which performs the scale and offset step of 822 in reverse, the reverted Cartesian position and velocity is input into the Cartesian controller at 820. At the Cartesian controller 820, the original Cartesian position and velocities as output from the FKIN controller 691 is compared with the Cartesian position and velocity input from the simulated domain 812. If no limitations were transgressed in the simulated domain 812 the velocity and position values input from the FKIN controller 691 would be the same as the velocity and position values input from the simulated domain 812. In such a case, a zero error signal is generated by the Cartesian controller 820.

In the event that the desired Cartesian slave position and velocity input at 811 would transgress one or more set limitations, the desired values are restricted to stay within the bounds of the limitations. Consequently, the Cartesian velocity and position forwarded from the simulated domain 812 to the Cartesian controller 820 would then not be the same as the values from the FKIN controller 691. In such a case, when the values are compared by the Cartesian controller 820, an error signal is generated.

The type of limitations imposed on the desired slave Cartesian position and velocity will be described in greater detail hereinbelow.

Assuming that a zero error is generated at the Cartesian controller 820 no signal is passed from the Cartesian controller or converter 820. In the case that an error signal is generated the signal is passed through a summation junction 827 to a master transpose kinematics controller 828.

The error signal is typically used to calculate a Cartesian force. The Cartesian force is typically calculated, by way of example, in accordance with the following formula:

$$F_{CART} = K(\Delta x) + B(\Delta \dot{x})$$

where K is a spring constant, B is a damping constant, $\Delta \dot{x}$ is the difference between the Cartesian velocity inputs to the Cartesian controller 820 and $\Delta x$ is the difference between the Cartesian position inputs to the Cartesian controller 820. It will be appreciated that for an orientational error, a corresponding torque in Cartesian space is determined in accordance with conventional methods.

The Cartesian force corresponds to an amount by which the desired slave position and/or velocity extends beyond the limitations imposed in the simulated domain 812. The Cartesian force, which could result from a velocity limitation, a positional limitation, and/or a singularity limitation, as described in greater detail below, is then converted into a corresponding torque signal by means of the master transpose kinematics controller 828 which typically includes a processor employing a Jacobian Transpose ($J^T$) matrix and kinematic relationships to convert the Cartesian force to a corresponding torque in joint space. The torque thus determined is then input to a processor at 830 whereby appropriate electrical currents to the motors associated with the master 700 are computed and supplied to the motors. These torques are then applied on the motors operatively associated with the master control 700. The effect of this is that the surgeon experiences a resistance on the master control to either move it at the rate at which he or she is urging the master control to move, or to move it into the position into which he or she is urging the master control to move. The resistance to movement on the master control is due to the torque on the motors operatively associated therewith. Accordingly, the higher the force applied on the master control to urge the master control to move to a position beyond the imposed limitation, the higher the magnitude of the error signal and the higher an opposing torque on the motors resisting displacement of the master control in the direction of that force. Similarly, the higher the velocity imposed on the master beyond the velocity limitation, the higher the error signal and the higher the opposing torque on the motors associated with the master.

Figure 15:
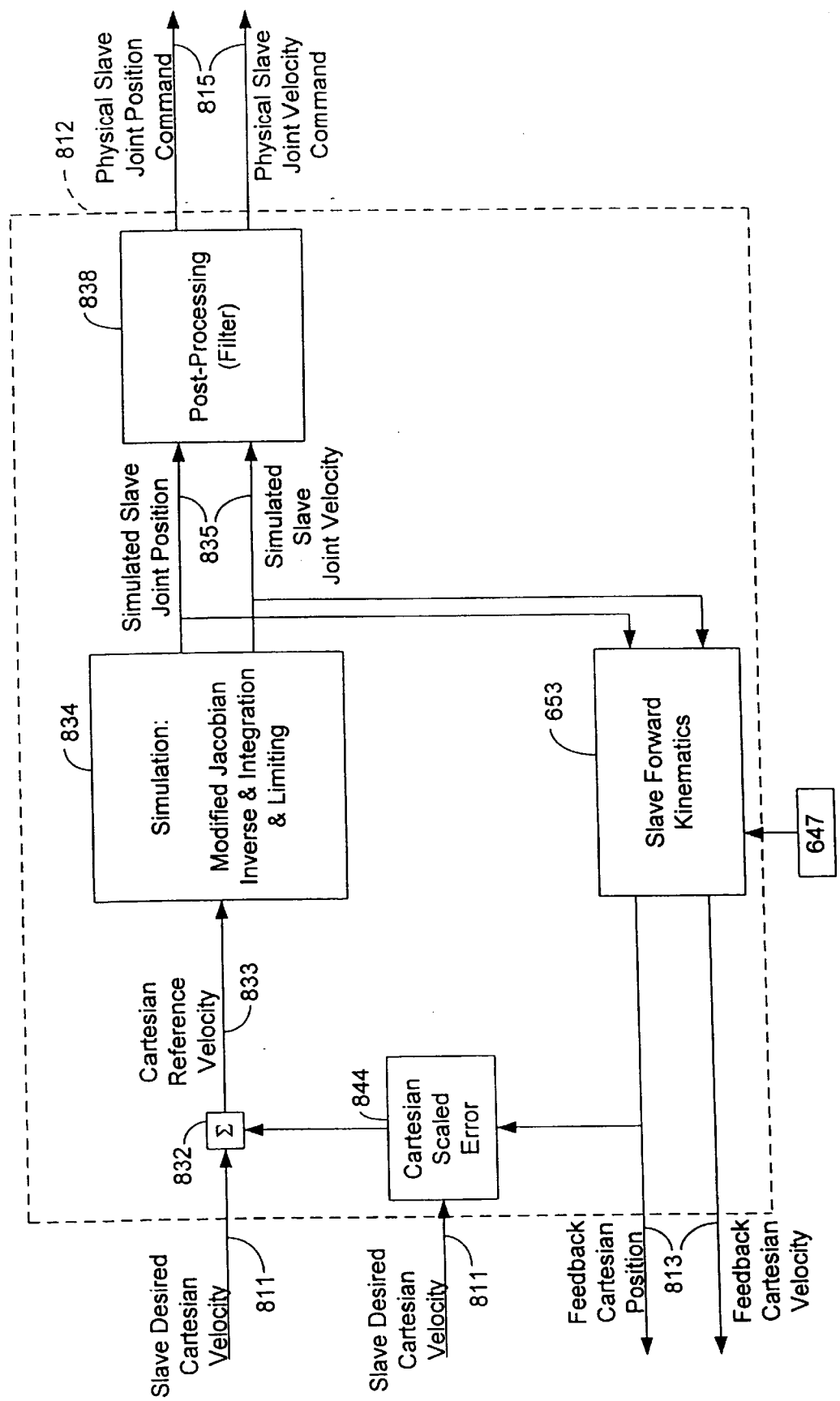
FIG. 15 shows further detail of a "simulated domain" of the control system shown in FIG. 14.

The imposition of the limitations in the simulated domain 812 will now be described in greater detail with reference to FIG. 15 of the drawings. In FIG. 15, like reference numerals are used to designate similar parts or aspects, unless otherwise stated.

The slave desired Cartesian velocity is passed from the scale and offset converter 822 through a summation junction at 832. It will be appreciated that the slave desired Cartesian velocity is passed through the summation junction 832 sequentially at the rate of the control system processing cycle, namely 1300 Hz. At the junction 832, an error signal is imparted on the slave desired Cartesian velocity when the desired velocity of a prior desired Cartesian velocity signal would have instructed the simulated slave to transgress one or more limitations. This will be described in greater detail hereinbelow. If the prior desired slave velocity would not have caused a transgression, no error signal would have been generated and the desired slave velocity would then pass through the summation junction 832 unchanged. The velocity signal passed from the summation junction 832 is referred to as Cartesian reference velocity as indicated by arrow 833.

From the summation junction 832, the Cartesian reference velocity is fed to a simulation block 834. The reference velocity is then compared with the limitations in the simulation block 834, as will be described in greater detail hereinbelow with reference to FIGS. 16 to 21 of the drawings.

In the case where the slave reference velocity does not transgress a limitation, the slave reference velocity passes through the simulation block 834 unchanged. However, a corresponding simulated slave joint velocity is computed in the simulation block 834.

The simulated joint velocity is integrated in the simulation block 834 to yield a corresponding simulated joint position. The simulated joint velocity and position is output from the simulation block 834 as indicated by arrows 835.

The simulated joint velocity and position is then passed through a filter at 838. The filter 838 is arranged to separate tremors from the velocity and position signals. It will be appreciated that such tremors could result from inadvertent shaking of the master control which can be induced on the master control by the surgeon. Since it would be desirable to remove such tremor movements from the actual slave velocity and position signals so as to enhance slave precisional movement in response to master input, these tremors are filtered from the velocity and position signals by means of the filter 838. After the filtering step at 838, resultant slave joint velocity and position signals are passed to the slave as indicated by arrows 815 and as will be described in greater detail hereinbelow. It will be appreciated that the simulated slave joint position and/or velocity signal can be modified in any required manner at 838. Typically, modifications not requiring feedback to the master can be implemented at 838. Thus, the filtering step 838 is not necessarily limited to filtering tremors from the signal only. In addition, or instead, the frequency of the position and/or velocity signals may be modified to inhibit resonance in the slave, for example.

Still referring to FIG. 15 of the drawings, the simulated joint velocity and position, after passing through the simulation block 834, is routed through an FKIN controller at 653 to compute corresponding velocities and positions in Cartesian space, as described with reference to FIG. 12 of the drawings. The signals are then passed to the Cartesian controller 820 as already described with reference to FIG. 14.

Still referring to FIG. 15, the position signal from the FKIN controller 653 is routed into a Cartesian scaled error block at 844. The desired Cartesian slave position derived from the scale and offset block 822 is also routed into the Cartesian scaled error block 844. The two signals are compared at 844 to compute an error signal should they not correspond. Should the two signals be equal, namely where the desired slave velocity signal was not restricted in the simulated domain 834, no error signal is generated.

In the case where the desired slave velocity was restricted in the simulation block 834, the simulated joint velocity output would not correspond with the reference Cartesian slave velocity input to the simulation block 834. Accordingly, after integration in the simulation block 834, and conversion to Cartesian space by the FKIN controller 653, the resultant corresponding Cartesian position would not correspond with the original desired Cartesian slave position input to the Cartesian scaled error block 844. Accordingly, an error signal of a magnitude determined typically by subtraction of the resultant Cartesian position from the original desired position and multiplication with an appropriate constant, is generated by the Cartesian scaled error block 844. This error signal is imposed on the next desired slave velocity signal at the summation junction 832.

It will be appreciated that only the velocity signal is input to the simulation block 834. Thus, limitations are imposed in a dynamic fashion in the simulation block. The simulated slave position does not necessarily track the master position simultaneously. This is particularly the case where a limitation has been imposed in the simulation block 834. For example, should a velocity limit have been imposed where the master was moved too quickly, a degree of lagging of the simulated slave position to catch up with the master position results. Accordingly, a discrepancy between the master and the slave positions ensues. By means of the positional error generated at 844, an appropriate velocity signal change is effected at the junction 852 to effect a positional "catch up" function on the velocity signal. Thus, should the master be brought to rest where a positional error is generated, the velocity signal input to 832 would be zero, but a Cartesian reference velocity would still be input to the simulation block 834 to effect the catching up of the simulated slave position with that of the master.

Referring once again to FIG. 14 of the drawings, the resultant slave joint velocity and position signal is passed from the simulated domain 812 to a joint controller 848. At the joint controller 848, the resultant joint velocity and position signal is compared with the current joint position and velocity. The current joint position and velocity is derived through the sensors on the slave as indicated at 849 after having been processed at an input processor 851 to yield slave current position and velocity in joint space.

The joint controller 848 computes the torques required on the slave motors to cause the slave to follow the resultant joint position and velocity signal taking its current joint position and velocity into account. The joint torques so determined are then routed to a feedback processor at 852 and to an output processor at 854.

The joint torques are typically computed, by way of example, by means of the following formula:

$$T = K(\Delta\theta) + B(\Delta\dot\theta)$$

where K is a spring constant, B is a damping constant, $\Delta\dot\theta$ is the difference between the joint velocity inputs to the joint controller 851, and $\Delta\theta$ is the difference between the joint position inputs to the joint controller 851.

The output processor 854 determines the electrical currents to be supplied to the motors associated with the slave to yield the commanded torques and causes the currents to be supplied to the motors as indicated by arrow 855.

From the feedback processor 852 force feedback is supplied to the master. As mentioned earlier, force feedback is provided on the master 700 whenever a limitation is induced in the simulated domain 812. Through the feedback processor 852 force feedback is provided directly from the slave 798, in other words, not through a virtual or simulated domain but through direct slave movement. This will be described in greater detail hereinbelow.

As mentioned earlier, the slave indicated at 798 is provided with a plurality of sensors. These sensors are typically operatively connected to pivotal joints on the robotic arm 10 and on the instrument 14.

These sensors are operatively linked to the processor at 851. It will be appreciated that these sensors determine current slave position. Should the slave 798 be subjected to an external force great enough to induce reactive movement on the slave 798, the sensors will naturally detect such movement. Such an external force could originate from a variety of sources such as when the robotic arm 10 is accidentally knocked, or knocks into the other robotic arm 10 or the endoscope arm 302, or the like. As mentioned, the joint controller 848 computes torques required to cause the slave 798 to follow the master 700. An external force on the slave 798 which causes its current position to vary also causes the required slave movement to follow the master to vary. Thus a compounded joint torque is generated by the joint controller 848, which torque includes the torque required to move the slave to follow the master and the torque required to compensate for the reactive motion induced on the slave by the external force. The torque generated by the joint controller 848 is routed to the feedback processor at 852, as already mentioned. The feedback processor 852 analyzes the torque signal from the joint controller 848 and accentuates that part of the torque signal resulting from the extraneous force on the slave 798. The part of the torque signal accentuated can be chosen depending on requirements. In this case, only the part of the torque signal relating to the robotic arm 12, 12, 302 joints are accentuated. The torque signal, after having been processed in this way is routed to a kinematic mapping block 860 from which a corresponding Cartesian force is determined. At the kinematic block 860, the information determining slave fulcrum position relative to the camera frame is input from 647 as indicated. In this regard refer to FIG. 12 of the drawings. Thus, the Cartesian force is readily determined relative to the camera frame. This Cartesian force is then passed through a gain step at 862 appropriately to vary the magnitude of the Cartesian force. The resultant force in Cartesian space is then passed to the summation junction at 827 and is then communicated to the master control 700 as described earlier.

Reference numeral 866 generally indicates another direct force feedback path of the control system 810, whereby direct force feedback is supplied to the master control 700. The path 866 includes one or more sensors which are not necessarily operatively connected to slave joints. These sensors can typically be in the form of force or pressure sensors appropriately positioned on the surgical instrument 14, typically on the end effector 58. Thus, should the end effector 58 contact an extraneous body, such as body tissue at the surgical site, it generates a corresponding signal proportionate to the force of contact. This signal is processed by a processor at 868 to yield a corresponding torque. This torque is passed to a kinematic mapping block 864, together with information from 647 to yield a corresponding Cartesian force relative to the camera frame. From 864, the resultant force is passed through a gain block at 870 and then forwarded to the summation junction 827. Feedback is imparted on the master control 700 by means of torque supplied to the motors operatively associated with the master control 700 as described earlier. It will be appreciated that this can be achieved by means of any appropriate sensors such as current sensors, pressure sensors, accelerometers, proximity detecting sensors, or the like.

As mentioned, the control system 810 enables limitations to be set in the simulation block 834. These limitations can be chosen to conform with mechanical system limitations or constraints and/or can be preset to correspond with environmentally-sensitive movement limitations at the surgical site as will be described in greater detail hereinbelow. Thus, the limitations imposed in the simulated domain 812, in one instance, can be regarded as virtual limitations corresponding with actual physical system limitations. The limitations at the simulated domain 812 are not derived from actual slave movement but from simulated or virtual slave movement. Thus, the slave is prevented from actually transgressing a limitation by simulating its movement and velocity and restricting the simulated movement and velocity before instructing the actual slave to respond. One typical limitation set in the simulated domain 812 concerns singularities of the system.

What is meant by the term singularity will now be described by way of an example of a singularity in the mechanical structure of the minimally invasive surgical apparatus. Referring to FIG. 2A of the drawings, and as already mentioned, the instrument 14 when mounted on the robotic arm 10 is linearly displaceable in the direction of arrow P. If the instrument 14 is positioned such that the end effector 58 is relatively far removed from the fulcrum 49 and the master control is manipulated to command responsive movements, the responsive movement of the slave can normally readily be performed. At a specific fixed distance from the fulcrum 49, the end effector has a range of lateral movement constrained within bounds dictated by constraints in the mechanical structure of the arm 12. It will be appreciated that the closer the end effector 58 is displaced toward the fulcrum 49, the smaller the possible range of lateral movement becomes. This can be visualized by picturing a cone having its apex at the fulcrum 49 and extending from the fulcrum 49 in a downward direction in FIG. 2A. The range of lateral movement of the end effector 58 being limited to within the visualized cone. It will thus be appreciated that toward the base of the visualized cone, e.g., a 1-inch lateral movement of the end effector, can normally readily be achieved by the mechanical structure of the arm 12. However, toward the apex of the cone, in other words toward the fulcrum 49, a point is reached where a 1-inch lateral movement of the end effector 58 is simply not achievable due to the mechanical constraints of arm 12. Furthermore, the movement by the robotic arm 12 to induce lateral movement of the end effector 58 becomes more radical the closer the end effector 58 is displaced toward the fulcrum 49.

When a surgeon is performing a surgical procedure by means of the minimally invasive surgical apparatus, he or she is normally unaware of the robotic arm 12 movements since he or she is viewing the surgical site through the viewer 202. Accordingly, unless provision is made to the contrary, it could happen that in the course of a surgical procedure the end effector 58 is displaced too near the fulcrum 49 so that master input causes the robotic arm 12 to move too quickly over corresponding long distances in responding to the commanded end effector movements. The control system 810 is arranged to provide a method of inhibiting the robotic arm from making too rapid or large a movement in response to master input because of the singularity described above.

Another singularity of the mechanical structure of the slave, in particular of the surgical instrument 14, will now be described with reference to FIG. 5 of the drawings.

As mentioned, the end effector 58 is angularly displaceable about axis 14.2 as indicated by arrows 59. Should the axis of symmetry 60A of the end effector be positioned along the axis 14.2, angular displacement of the end effector about axis 60A is readily induced. However, should the axis 60A be positioned perpendicular to the axis 14.2, angular displacement of the end effector 58 about axis 60A is not possible. Thus, a singularity is approached as the axis 60A approaches a position perpendicular to the axis 14.2.

A further singularity of the robotic arm 10, can be understood with reference to FIG. 4 of the drawings. As already mentioned, the robotic arm is angularly displaceable about axis 28 as indicated by arrows 26. When the axis 14.2 is perpendicular to the axis 28, movement of the arm 10 in the direction of arrows 26 is readily induced on the end effector 58. As will readily be observed in FIG. 4, a singularity is approached the closer the axis 14.2 is moved toward a position parallel to the axis 28.

Another typical limitation imposed in the simulated domain 812 relates to positional constraints of the various joints.

Another typical limitation imposed in the simulated domain is a velocity limitation corresponding to practicably mechanically achievable slave velocity. Naturally, the slave has greater mass and moments of inertia than the master. Thus, should the surgeon move the master too quickly, or should the master accidentally be knocked to induce rapid movement thereon, the slave would be commanded to move in sympathy with the master but at a rate not practicably achievable by the arm 10 due to mechanical constraints.

As mentioned, optionally, limitations relating to surgical environmental constraints can also be effected as described in greater detail hereinbelow.

Figure 16:
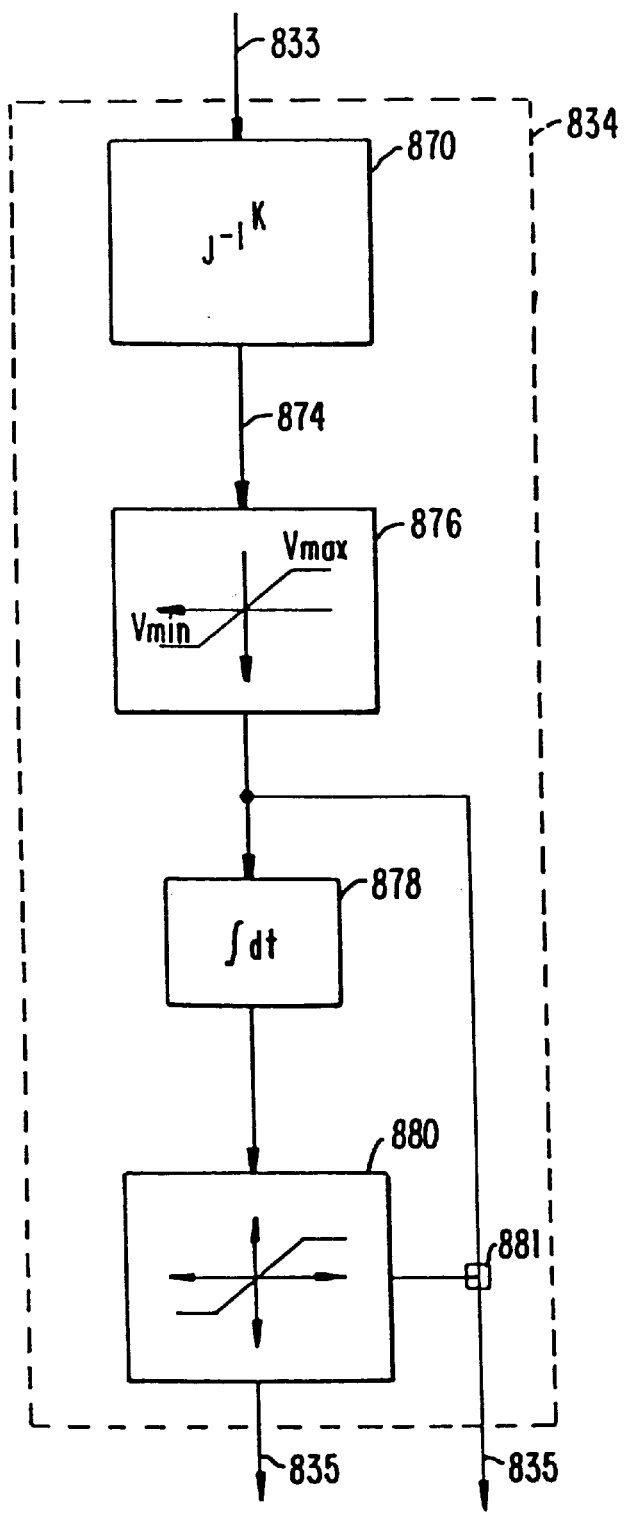
FIG. 16 shows one embodiment of a simulation block shown in FIG. 15.

Referring now to FIG. 16 of the drawings, one embodiment of the simulation block 834 includes a modified Jacobian inverse controller indicated by $J^{-1*}$ at 870. The modified Jacobian inverse controller is arranged to inhibit the detrimental effects which result when a singularity is approached. This is achieved by modifying a Jacobian inverse matrix of the controller $J^{-1*}$. The modification to the matrix will now be described by way of example and with reference to FIGS. 2A and 17 of the drawings.

Figure 17:
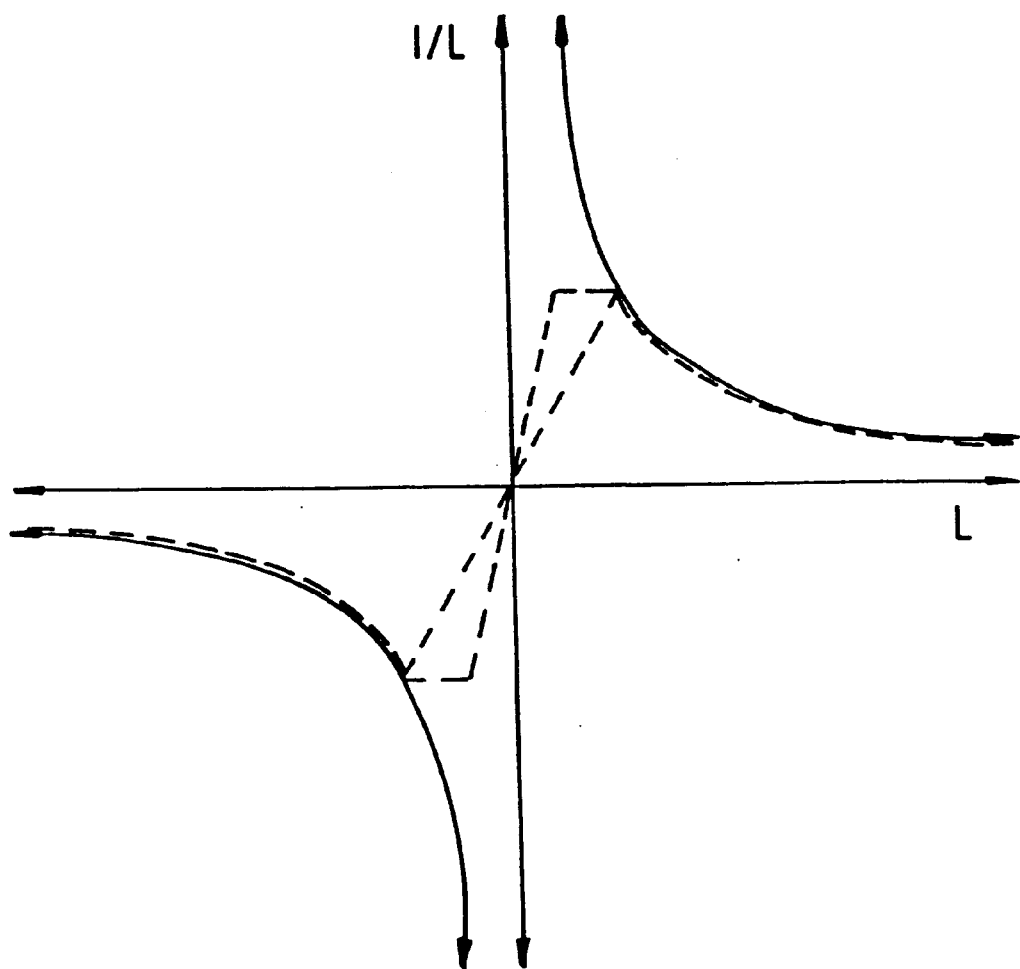
FIG. 17 shows a relationship between L and 1/L.

In FIGS. 2A and 17, the length of the arm portion of the shaft 14.1 of the instrument 14 which extends beyond the fulcrum 49 is indicated by L.

The relationship between velocity $\dot{x}$ in Cartesian space relative to angular velocity $\dot{\theta}$ in joint space is typically expressed by the relationship $$\dot{x} = J.\dot{\theta}$$

For the minimally invasive surgical apparatus, the Jacobian matrix is typically in the Form of a 6×6 term matrix for converting joint space coordinates to corresponding Cartesian coordinates. Naturally, some of the terms in the matrix include a multiplication factor equal to L. Accordingly, when it is required to determine positions in joint space corresponding to Cartesian coordinates, the following relationship is used:

$$\dot{\theta} = J^{-1}.\dot{x}$$

When the inverse Jacobian matrix is used in this fashion, the terms including the multiplication factor of L become terms having a multiplication factor of 1/L.

It will be appreciated that as L decreases the term 1/L approaches infinity. This characteristic associated with a singularity is schematically illustrated in FIG. 17. The length L is indicated along the horizontally extending axis and the corresponding factor 1/L is indicated along the vertically extending axis. The parabolic lines indicate the relationship between L and 1/L. It is clear that when the required joint velocity is determined by means of the Cartesian velocity $\dot{x}$ and a term includes the multiplication factor 1/L, the joint velocity approaches infinity as the value of L decreases, thus as the end effector is moved closer to the fulcrum 49.

To compensate for these detrimental effects when a singularity is approached, the 1/L term in the Jacobian Inverse matrix is replaced with a function of L which yields a resultant relationship between L and 1/L as indicated in dashed lines in FIG. 17. Two dashed lines are indicated to show different possible functions of L. In similar fashion the Jacobian Inverse matrix is modified to cater for all the singularities of the system already described.

Referring again to FIG. 16 of the drawings, the simulation block 834 will now be described in further detail.

The modified Jacobian Inverse controller which makes allowance for singularities as hereinbefore described is indicated by the reference numeral 870. The Cartesian space reference velocity is input as indicated by arrow 833. After conversion to a resulting joint velocity by the controller 870, the resultant joint velocity is output at 874. The resultant joint velocity 874 is then input to a joint velocity limitation step at 876. At this step the resultant joint velocity is limited to remain within a range between a predetermined maximum velocity $V_{max}$, and a predetermined minimum velocity $V_{min}$. These maximum and minimum values are typically selected to constrain the joint velocity within limitations corresponding to constraints of the mechanical structure of the system. Accordingly, at 876, should the joint velocity input 874 have a magnitude greater than the maximum and minimum values, the joint velocity magnitude 874 is decreased to within the set range. Thus:

if $\dot{\theta}$>max $\dot{\theta}$=max if $\dot{\theta}$<(min) $\dot{\theta}$=(min)

where $\dot{\theta}$ represents joint velocity, and max denotes a positive magnitude and min denotes a negative magnitude.

After the joint velocity is limited in this manner, the joint velocity is integrated at 878 to yield a corresponding position in joint space. In similar fashion to the joint velocity limitation step at 876, the position is limited at 880 to remain within a set positional range.

Figure 14:
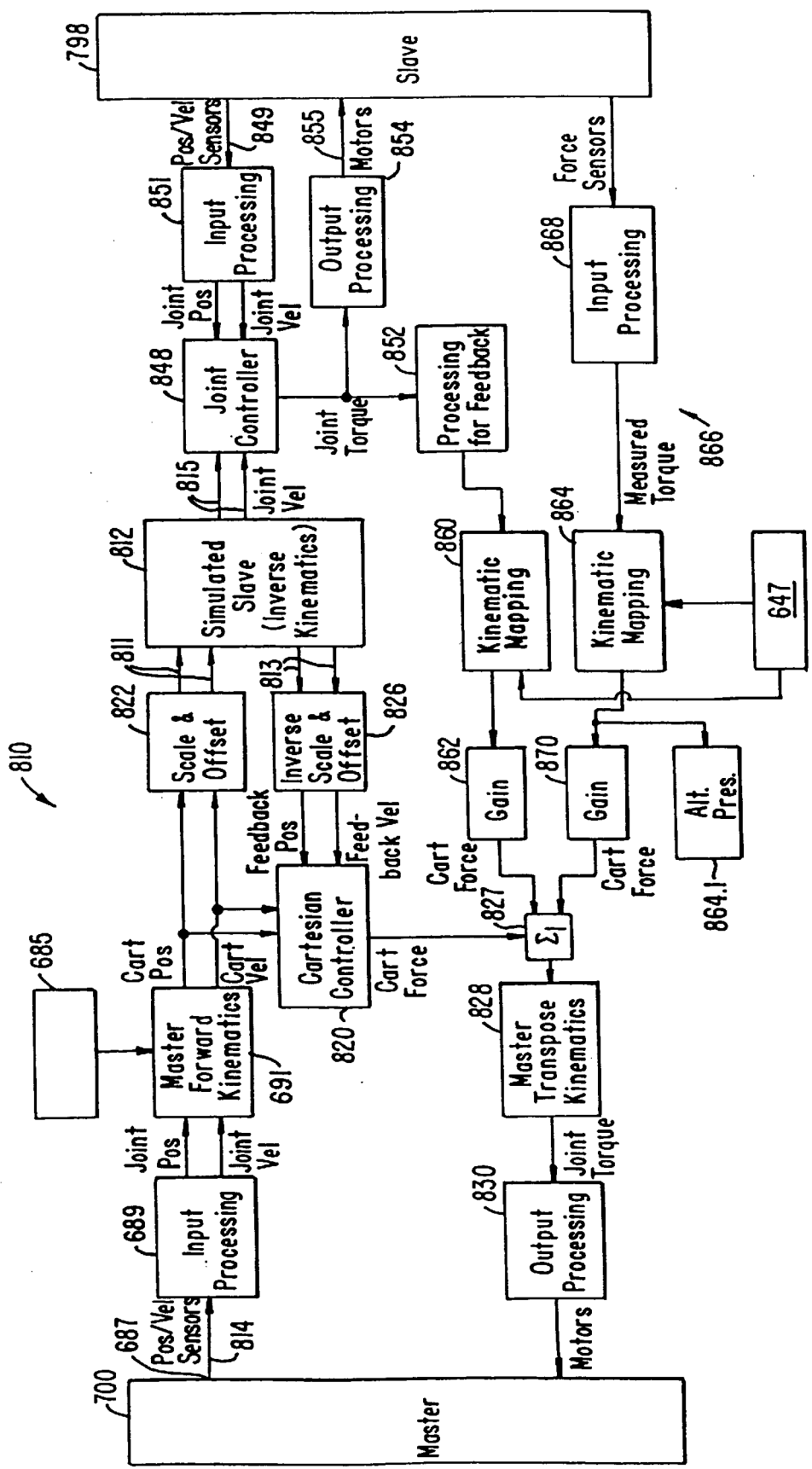
FIG. 14 shows a block diagram representing control steps followed by the control system of the minimally invasive surgical apparatus in effecting control between pincher formation positional and orientational movement and end effector positional and orientational movement.

From 880, the resultant joint positional signal is routed to the filter 838 as indicated by one of the arrows 835 and as already described herein with reference to FIG. 14. The resultant velocity signal as output from 876 is routed to the filter 838 as indicated by the other arrow 835. The resultant velocity signal is linked to the positional control step 880, as indicated at 881, so that in the event that the position is limited, the velocity signal is rendered zero.

As mentioned, velocity, position and singularity limitations or constraints are applied to the Cartesian reference velocity in the simulation block 834 indicated in FIG. 14 to yield a simulated slave joint position and velocity. Naturally, should the Cartesian reference velocity input to the simulation block 834 not result in a transgression of any of the limitations set for the slave, the Cartesian reference velocity input to the simulation block 834 is then simply transferred into corresponding slave joint position and velocity signals without any imposition of limitations. The corresponding slave joint position and velocity is then forwarded to the slave after the filtering step at 838.

An alternative simulation block 834B and another method of imposing limitations will now be described with reference to FIG. 18 of the drawings in which like reference numerals are used to designate similar parts unless otherwise indicated.

Figure 18:
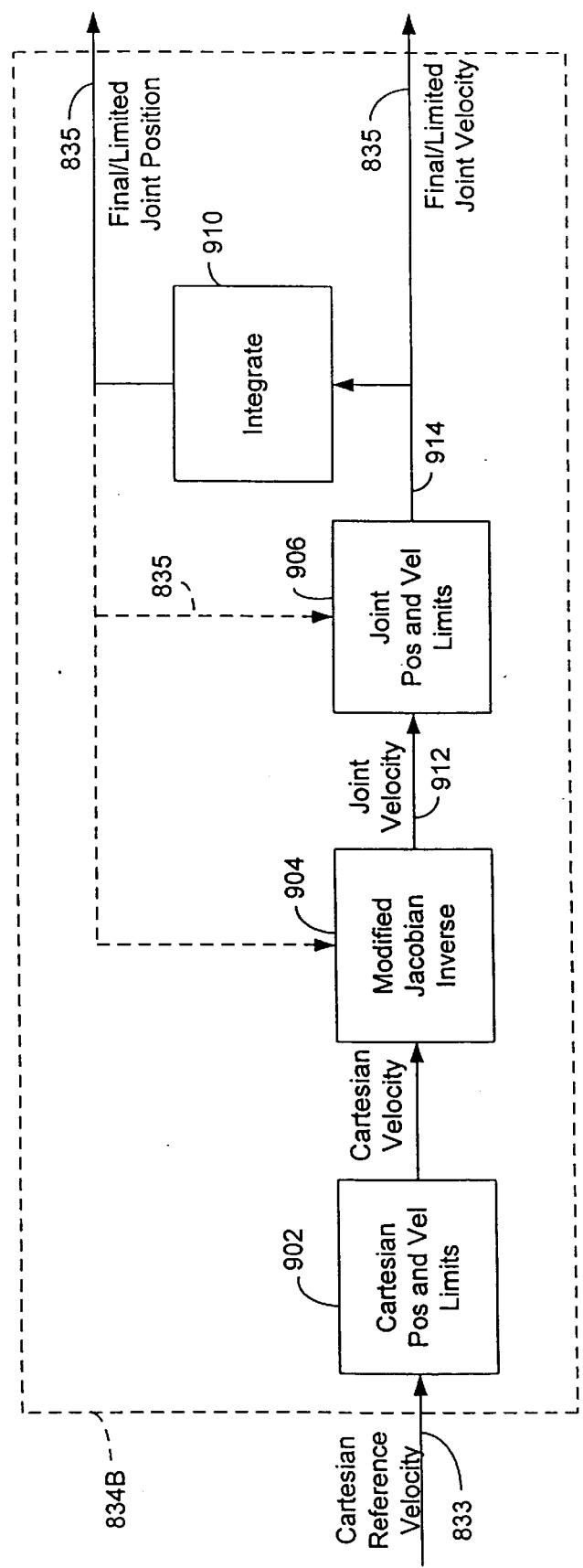
FIG. 18 shows another embodiment of the simulation block shown in FIG. 15.

Referring now to FIG. 18, and in the simulation block 834B, the Cartesian reference velocity is initially input into a Cartesian position and velocity limit block at 902. At 902, any desired limitations to position and velocity in Cartesian space can be set. This can be achieved in similar fashion to the manner in which the joint velocity and position limitations were imposed in FIG. 16. Such limitations can be chosen to suit the specific surgical procedure to be performed. Thus, for example, should the surgical procedure to be performed be at a sensitive location, such as close to the brain, or heart, or the like, limitations can be set to constrain end effector movement within a space so as not to be able to contact the area of sensitivity. Thus, at 902, limitations can be tailored to meet specific environmental limitations defined by the specific surgical procedure to be performed so as to avoid accidental damage to a sensitive organ, or the like. Thus, at 902, slave position and velocity can be restricted to remain within preset limitations dictated by the surgical procedure to be performed. It will be appreciated that such surgical environment dependent limitations can be imposed in the simulation block 834 in FIG. 16, and also in the preferred simulation block 834A to be discussed with reference to FIG. 20.

After the limitation step at 902, the resultant Cartesian velocity is input to a modified Jacobian Inverse controller at 904. The modified controller 904 imposes limitations on the Cartesian velocity input during conversion of the Cartesian velocity input into a corresponding joint space velocity to make allowance for singularities as already described.

From the modified Jacobian Inverse controller 904, the resultant joint velocity is input into a joint position and velocity block at 906. At the joint position and velocity block 906, the joint velocity input is monitored to ensure that corresponding velocity and position commands to each specific joint would not transgress set limitations corresponding to actual angular position and velocity limitations of that joint. After the joint velocity has been monitored at 906, and any limitations imposed, the resultant simulated slave joint velocity is output as indicated by arrow 835. The simulated slave joint velocity is also fed through an integration step at 910 to yield the corresponding simulated slave joint position.

The simulated joint position for each specific joint is routed to the joint position and velocity block 906, and the modified Jacobian Inverse block 904 as indicated in dashed lines. The position signal 835 is routed to the modified Jacobian Inverse block 904 to enable transformation from Cartesian to joint space. The position signal 835 is routed to the position and velocity block 906 in order that joint position and velocity limits can be imposed at 906. This will now be described with reference to FIG. 19 in which like reference numerals are used to designate similar parts unless otherwise indicated. It will be appreciated that FIG. 19 exemplifies the imposition of positional and velocity limits on a single joint. The same method of imposing such positional and velocity limits is employed for each joint at 906.

Figure 19:
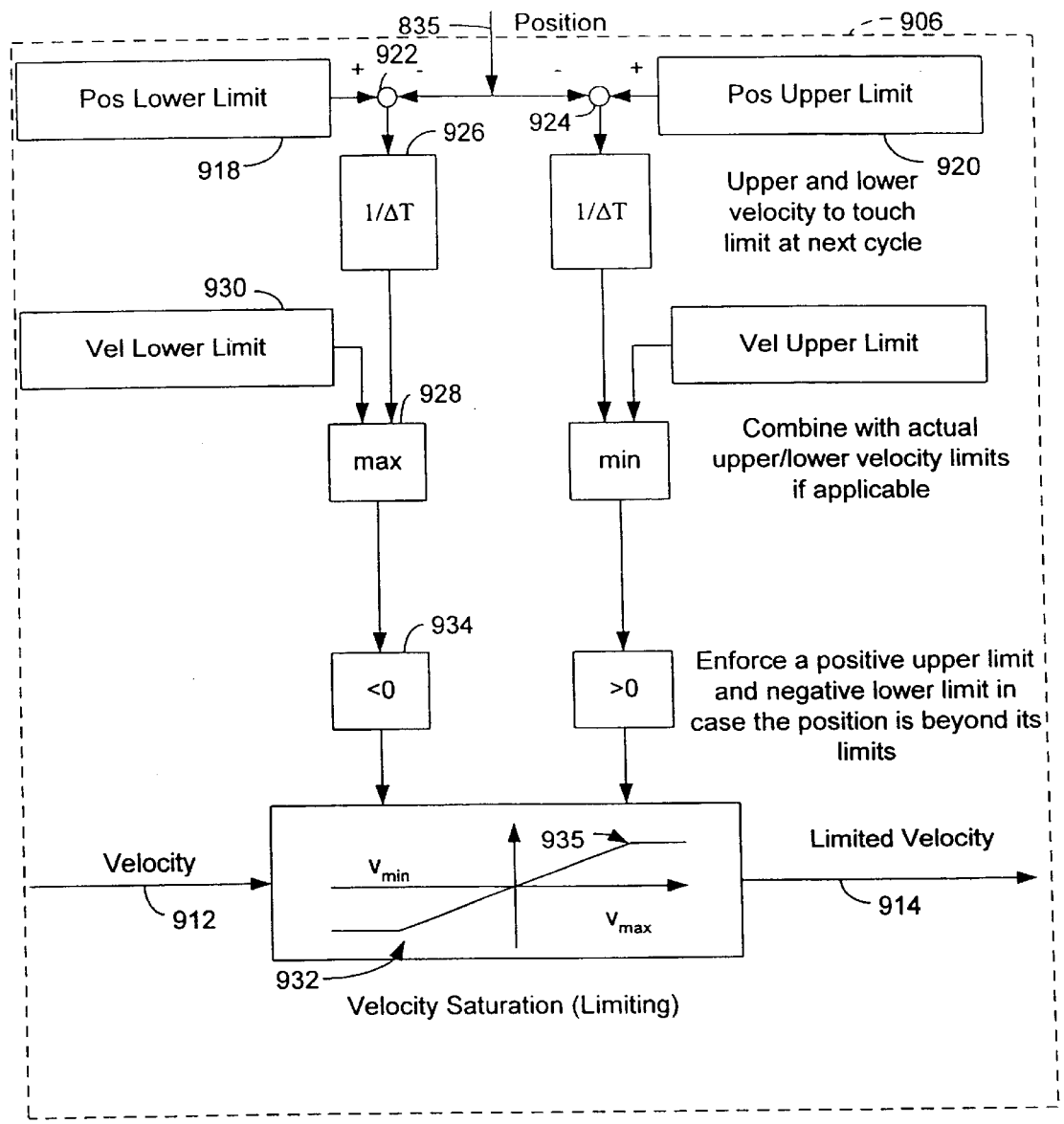
FIG. 19 shows a block diagram indicating the imposition of simulated velocity and position limits.

In FIG. 19, the joint velocity input from the modified Jacobian Inverse controller at 904 is indicated by arrow 912. The resultant velocity after having passed through the joint position and velocity block is indicated by arrow 914 and the joint position input is indicated by arrow 835 and is shown in dashed lines. The joint for which position and velocity limits are to be imposed by the block diagram shown in FIG. 19 normally has physical limitations. Thus, the joint has a maximum position in which the arm members which are pivotally connected thereby are at a maximum angular position relative to each other. Similarly, the joint has a minimum position in which the arm members which are connected one to another thereby are at a minimum angular position relative to each other. Accordingly, the joint has an angular displacement range extending between its minimum and its maximum position. The angular limits of the joint are indicated by blocks 918 and 920, respectively, block 918 indicating the minimum position and block 920 the maximum position. Naturally, since we are dealing with a simulated domain, the limits can be chosen to suit. Accordingly, the minimum and maximum angular positions 918, 920 need not necessarily correspond with the actual physical positional limits of the joint, but can be chosen at any appropriate angular positions within the angular positional range capabilities of the joint.

The position input at 835 is normally varying continually as the surgeon manipulates the master during the course of a surgical procedure. The positional input 835 is fed to the summation junctions 922, 924. At the junction 922, the angular position as input at 835 is compared with the positional minimum or lower limit to yield an angular value corresponding to the angular deviation of the position input 835 relative to the limit 918. Thus, at 922, an angular value equal to the difference between the angular limit and the angular position input 835 is determined. The angular deviation from the lower limit 918 thus determined, is then fed to a velocity determination block at 926. The processing cycle rate of the control system is known. In this case, it is typically 1300 Hz. At 926, the velocity which the joint needs to have to cause its position to coincide with the lower joint limit 918 at the next processing cycle is determined. This velocity value is then routed to a decision block at 928. Naturally, if the angular position as input at 835 is far removed from the lower limit 918, the resultant velocity value derived at 926 will be very large, and typically physically unattainable. However, as the angular deviation approaches zero, namely, where the angular position 835 approaches the lower limit 918, the velocity output from 926 becomes less than the attainable joint velocity and becomes zero where the angular position 835 is at the lower limit 918.

Reference numeral 930 represents a set joint velocity limit. This limit is typically chosen in accordance with the acceptable joint velocity limit of that joint. This set velocity lower limit is also fed into the decision block 928. At 928 the two joint velocities are compared and the largest of the two selected. It will be appreciated that the largest value is selected because we are regarding a velocity limit in a negative direction. Thus, the largest value is the same as the smallest absolute value. The selected velocity value thus determined defines the lower velocity limit as indicated at 932.

It could happen that the joint is positioned beyond the positional lower limit 918. This can occur when the minimally invasive surgical apparatus is initially setup, or where the positional limits are selectively changed, for example. In such a case, it is desirable to cause the joint position to return to within the range set by the upper and lower limits at 918 and 920, respectively. For the lower angular position limit, this is achieved by the block 934. In essence, what is achieved by the block 934, is a constant curbing of positional movement beyond the lower limit. Thus, as the surgeon manipulates the master, movements causing the angular position of the joint to move toward the limit are permitted, but once such movement has taken place, the joint is restricted to its new position closer to the limit. The process is maintained until the joint position is within the range set by the values at 918, 920, respectively.

It will be appreciated that a maximum velocity, as indicated by reference numeral 935 is determined in similar fashion as the minimum velocity, as can be seen in FIG. 19 of the drawings.

Figure 20:
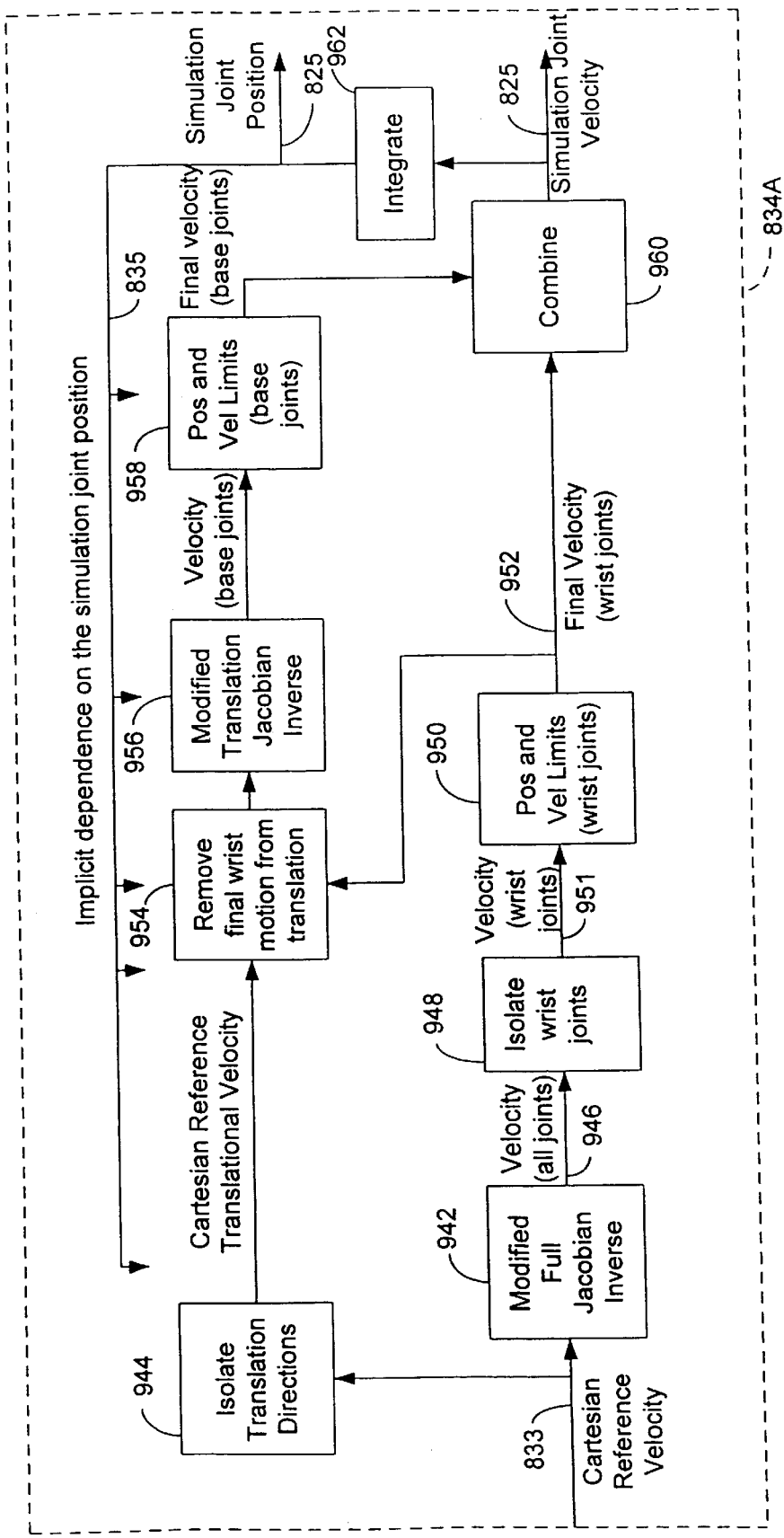
FIG. 20 shows a preferred embodiment of the simulation block shown in FIG. 15.

Referring now to FIG. 20 of the drawings, a preferred simulation block 834A will now be described. In FIG. 20 the same reference numerals are used to designate similar parts or aspects unless otherwise stated.

In FIG. 20, the Cartesian reference velocity is input as indicated by arrow 833. The simulated joint positions and velocities are output at 835. The Cartesian reference velocity 833 is routed to a modified full Jacobian Inverse block at 942 and to an isolation block at 944.

At 942, the Cartesian reference velocity signal 833 is transformed into a corresponding joint velocity signal 946. The modified full Jacobian Inverse block 942 makes allowance for singularities as already described with reference to 904 in FIG. 18.

In the minimally invasive surgical apparatus under discussion, the modified full Jacobian Inverse block typically includes a six by six term matrix. After transformation at the block 942, the resultant joint velocity signal is passed to an isolation block 948. At the isolation block 948, the terms relating to the wrist joints, as indicated in FIG. 5 of the drawings, are isolated from the terms relating to the joints on the robotic arm 12, as indicated in FIGS. 2A and 2B. After isolation at 948, the wrist joint velocities are forwarded to a wrist joint velocity and position limitation block at 950.

At 950 wrist joint velocity limits are imposed on each wrist joint in similar fashion to the method described above with reference to FIG. 19. However, for the wrist joints, namely the joints providing the three degree of freedom of movements to the end effector 58, the limitations are imposed simultaneously rather than on a joint by joint basis. This will now be described with reference to FIG. 21.

Figure 21:
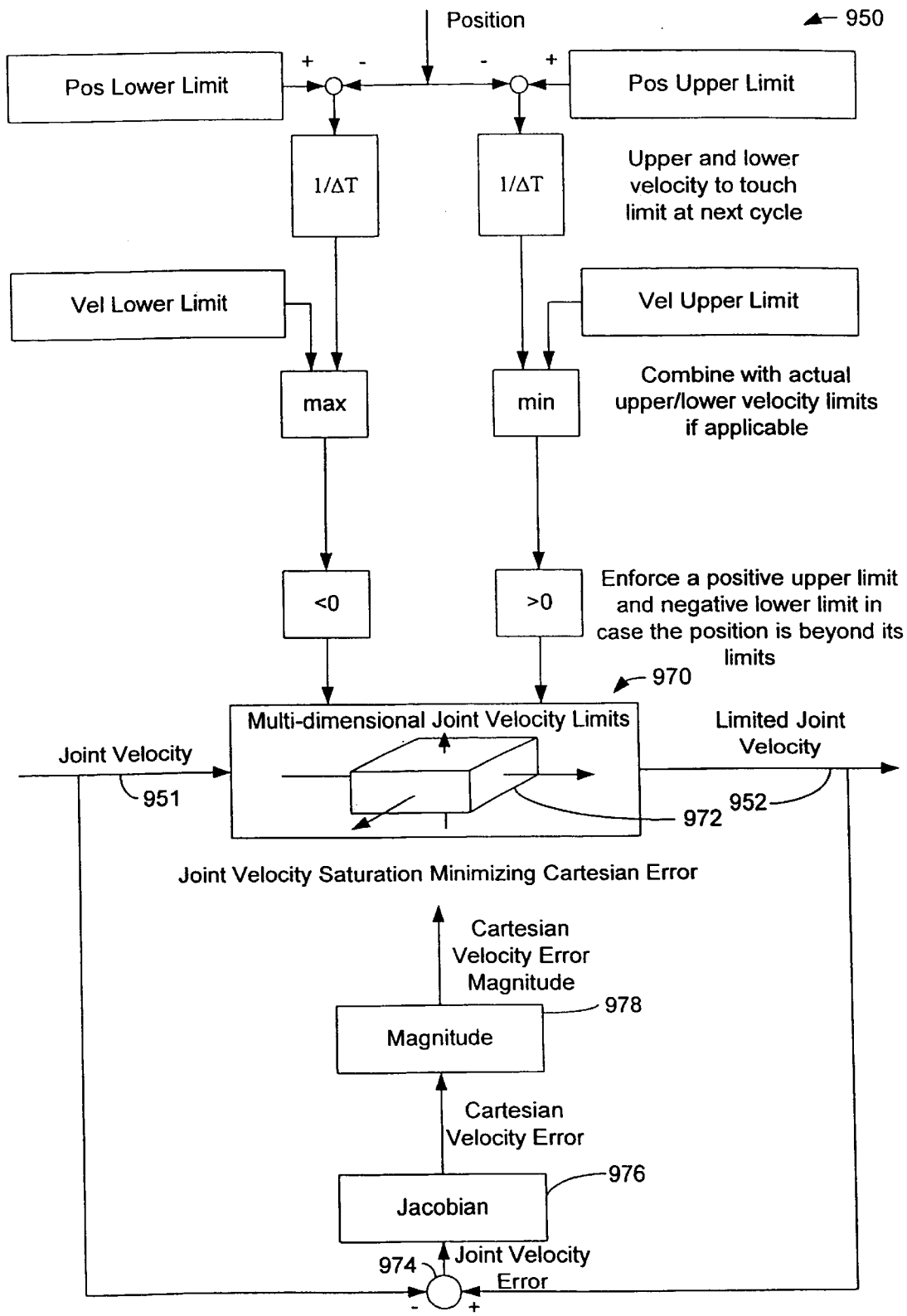
FIG. 21 shows a block diagram indicating the imposition of simulated velocity and position limits relating to orientational slave movement.

Referring to FIG. 21, the limits for each joint are determined in similar fashion to that described with reference to FIG. 19. But, as indicated at 970, the limitations are used to define a corresponding velocity limitation for the three joints together as indicated by the box 972. Accordingly, a multidimensional joint velocity limitation, in this case a three-dimensional joint velocity limitation, is provided.

The input joint velocity signal at 951 is compared to the multidimensional joint velocity limitation, at 970. Should the input velocity signal 951 fall entirely inside the limitation, it is unchanged by the limitation. In such a case the output velocity signal 952 is the same as the input velocity signal 951. However, should the input velocity signal 951 fall outside the limitation, the limitation block at 970 will select the output velocity 952 according to a criterion, which will now be described.

A joint velocity error between the input velocity signal 951 and the selected output velocity 952 is defined as illustrated at 974. The joint velocity error is transformed into a Cartesian velocity error using a Jacobian matrix at 976. It will be appreciated that the Jacobian matrix at 976 describes the kinematics of the wrist joints, which includes pivots 54, 60 and axis 14.2, with reference to FIG. 5. The magnitude of the Cartesian velocity error is then determined at 978.

The criterion for selection of the output velocity 952 by the limitation block 970 is the obedience of the multidimensional limitation and the minimization of the Cartesian velocity error magnitude.

Returning now to FIG. 20 the drawings, the output 952 from the limitation block 950 represents a combined joint velocity signal including joint velocities at the joints or pivots 54, 60 and joint velocity about axis 14.2, with reference to FIG. 5 of the drawings, after any limitations relating to velocity, position and singularities have been imposed.

At the isolation block 944, the translational Cartesian velocity terms are isolated from the Cartesian reference velocity signal 833. The isolated terms correspond to the Cartesian velocity commands addressing the joints on the robotic arm 12. After isolation, the Cartesian reference velocity signal for the outer joints only is forwarded to an adjustment block at 954.

In the event that the wrist joint velocity signal was restricted at one or both of the blocks 942, 950, the outer joint velocity can be adapted at 954. This will now be described in greater detail and with reference to FIG. 5 of the drawings.

It will be appreciated that a command at the master control 700 relating to only an orientation change of the end effector 58 can result in not only responsive angular movement about pivots 54, 60 and about axis 14.2 but also responsive outer joint movement. This is so because of structural dissimilarities between master and slave. Thus, for the slave to perform an orientational movement corresponding to a master orientational movement, it is sometimes required for the slave outer joints to move also.

Accordingly, in the event that wrist joint velocity limits were imposed, it is required to adapt outer joint, or translational, velocity to the extent to which the outer joint velocity formed part of the orientational wrist limitation. This is achieved at 954.

The resultant, possibly adapted, translational Cartesian velocity signal is then forwarded to a modified translation Jacobian Inverse block at 956. At 956, the signal is converted into a corresponding joint space velocity signal. The modified Jacobian Inverse matrix at 956 makes allowance for the fulcrum 49 singularity and the maximum robotic arm pitch singularity as already described with reference to FIG. 4. The joint space velocity signal from 956 is then passed to a limitation block at 958. At 958 positional and velocity limitations are imposed on the signal in a manner similar to that already described with reference to FIG. 19 or FIG. 21 of the drawings, and for each outer joint.

The final wrist joint velocity signal and the final outer joint velocity signal are then combined at 960 to yield the simulated joint velocity 835. The simulated joint velocity 835 is integrated at 962 to yield a corresponding simulated joint position, indicated by the other of the arrows 835.

The simulated joint position is fed to the blocks 942, 950, 954, 956 and 958 to enable the required computations.

While this invention has been particularly shown and described with references to preferred embodiments thereof, it will be understood by those skilled in the art that various changes in form and details may be made thereto without departing from the spirit and scope of the invention as defined in the accompanying claims. Where reference is made to Cartesian coordinates, polar coordinates, or cylindrical coordinates, or the like, may be used instead.

What is claimed is:

1. A surgical method including:
    generating a desired surgical instrument movement command signal by moving a master control with a movement from a first location to a second location, the desired surgical instrument command signal corresponding to the movement of the master control from the first location to the second location, wherein generating a desired surgical instrument movement command signal comprises generating a desired surgical instrument velocity signal relative to a coordinate reference system;

transforming the desired surgical instrument velocity signal relative to the coordinate reference system to a corresponding signal in joint space;

comparing the desired surgical instrument velocity signal in joint space with at least one preset surgical instrument movement limitation in joint space, wherein the at least one preset surgical instrument movement limitation comprises a preset surgical instrument velocity limitation in joint space;

restricting the desired surgical instrument movement command signal to yield a restricted surgical instrument movement command signal in response to the desired surgical instrument movement command signal transgressing the preset surgical instrument movement limitation;

moving a surgical instrument in response to the restricted surgical instrument movement command signal; and resisting the master control movement from the first location to the second location in response to the restricting of the desired surgical instrument command signal;

wherein the restricting step includes restricting the desired surgical instrument velocity signal in joint space to remain within a joint space velocity range extending between a minimum joint space velocity limit in a first direction and a maximum joint space velocity limit in a second direction in response to the desired surgical instrument velocity signal falling outside the range, to yield a resultant surgical instrument velocity signal in joint space;

and wherein the comparing step includes monitoring the surgical instrument position signal in joint space within a preset surgical instrument position limitation range extending between a maximum position and a minimum position, and in which monitoring the surgical instrument position signal within the preset surgical instrument position limitation range includes determining a corresponding joint space velocity required for the surgical instrument position to correspond with the maximum and the minimum positions during a next processing cycle.

2. A surgical method as claimed in claim 1, which includes comparing the joint space velocity required for the surgical instrument position to correspond with the maximum and the minimum positions with respectively a set maximum and a set minimum velocity.

3. A surgical method as claimed in claim 1, in which the transforming step is arranged to cause the desired surgical instrument velocity signal relative to the coordinate reference system to be transformed into joint space while limiting the desired surgical instrument velocity signal to account for at least one singularity.

4. A surgical method as claimed in claim 2, which includes maintaining the set maximum and the set minimum velocity values in response to the joint space velocity for the surgical instrument position to correspond with the maximum and the minimum positions being respectively greater than and less than the set maximum and the set minimum velocity values.

5. A surgical method as claimed in claim 2, which includes replacing the set maximum velocity value with the value of the joint space velocity for the surgical instrument position to correspond with the maximum position in response to the joint space velocity for the surgical instrument position to correspond with the maximum position being less than the set maximum velocity value.

6. A surgical method as claimed in claim 2, which includes replacing the set minimum velocity value with the value of the joint space velocity for the surgical instrument position to correspond with the minimum position in response to the joint space velocity for the surgical instrument position to correspond with the minimum position being greater than the set minimum velocity value.

7. A surgical method as claimed in claim 3, in which the conversion relationship is defined by a conversion matrix.

8. A surgical method as claimed in claim 3, in which the conversion relationship includes at least one term corresponding to the singularity, the method including modifying the term.

9. A surgical method as claimed in claim 6, in which transformation of the desired surgical instrument velocity signal includes employing a conversion relationship.

10. A surgical method as claimed in claim 9, in which the conversion matrix is an Inverse Jacobian matrix.

* * * * *

UNITED STATES PATENT AND TRADEMARK OFFICE
CERTIFICATE OF CORRECTION

PATENT NO. : 6,772,053 B2  Page 1 of 1
APPLICATION NO. : 10/269336
DATED : August 3, 2004
INVENTOR(S) : Günter D. Niemeyer It is certified that error appears in the above-identified patent and that said Letters Patent is hereby corrected as shown below:

On the title page, item [73] should read:

(73)  Assignee:  Intuitive Surgical, Inc., Sunnyvale CA (US) as recorded on July 6, 1999

Signed and Sealed this

Second Day of September, 2008

JON W. DUDAS
*Director of the United States Patent and Trademark Office*